United States Patent
Coiner et al.

(10) Patent No.: US 11,369,736 B2
(45) Date of Patent: Jun. 28, 2022

(54) CANNULA INSERTION AND RETRACTION MECHANISMS

(71) Applicant: AMGEN INC., Thousand Oaks, CA (US)

(72) Inventors: Erich Coiner, Poway, CA (US); Paul Faucher, Escondido, CA (US); Adam B. McCullough, Westlake Village, CA (US); Antonio Ubach, Tucson, AZ (US)

(73) Assignee: AMGEN INC., Thousand Oaks, CA (US)

( * ) Notice: Subject to any disclaimer, the term of this patent is extended or adjusted under 35 U.S.C. 154(b) by 231 days.

(21) Appl. No.: 16/485,245

(22) PCT Filed: Feb. 13, 2018

(86) PCT No.: PCT/US2018/017904
§ 371 (c)(1),
(2) Date: Aug. 12, 2019

(87) PCT Pub. No.: WO2018/152073
PCT Pub. Date: Aug. 23, 2018

(65) Prior Publication Data
US 2019/0365986 A1  Dec. 5, 2019

Related U.S. Application Data

(60) Provisional application No. 62/460,501, filed on Feb. 17, 2017.

(51) Int. Cl.
*A61M 5/142* (2006.01)
*A61M 5/158* (2006.01)
*A61B 17/34* (2006.01)

(52) U.S. Cl.
CPC ........ *A61M 5/14248* (2013.01); *A61M 5/158* (2013.01); *A61B 17/3421* (2013.01);
(Continued)

(58) Field of Classification Search
CPC .... A61M 5/14248; A61M 2005/14256; A61M 2005/1583; A61M 2005/1585;
(Continued)

(56) References Cited

U.S. PATENT DOCUMENTS

2004/0092875 A1  5/2004  Kochamba
2006/0135913 A1  6/2006  Ethelfeld
(Continued)

FOREIGN PATENT DOCUMENTS

WO  WO-2008024810 A2  2/2008
WO  WO-2015164649 A1  10/2015
(Continued)

OTHER PUBLICATIONS

International Search Report for International Application PCT/US2018/017904, dated Jun. 6, 2018.
(Continued)

*Primary Examiner* — Kami A Bosworth
*Assistant Examiner* — Emily J Becker
(74) *Attorney, Agent, or Firm* — Marshall, Gerstein & Borun LLP

(57) ABSTRACT

An insertion mechanism for a wearable drug delivery device that deploys a small gauge flexible cannula with support of a coaxial rigid trocar or hollow needle. After insertion, the trocar or hollow needle is withdrawn leaving the cannula in place for drug delivery. The insertion mechanism may also include an insertion mechanism housing having a proximal and distal end, a manifold configured to fluidly connect the hollow interior of the cannula and the fluid pathway connector, and a manifold guide carrying the manifold and movable between a first position and a second position. A hub carries the trocar and is removably connected to the manifold guide. An insertion biasing member may be initially retained in an energized state between the proximal end of the insertion mechanism housing and the hub, and a retraction biasing member may be initially retained in an energized state between the hub and the manifold guide.

15 Claims, 20 Drawing Sheets

(52) U.S. Cl.
CPC ............. *A61M 2005/14256* (2013.01); *A61M 2005/1583* (2013.01); *A61M 2005/1585* (2013.01)

(58) Field of Classification Search
CPC ......... A61M 2005/14252; A61M 2005/14268; A61B 17/3421
See application file for complete search history.

(56) References Cited

U.S. PATENT DOCUMENTS

| | | | |
|---|---|---|---|
| 2015/0057613 A1* | 2/2015 | Clemente et al. | ............................ A61M 5/14248 604/148 |
| 2016/0082182 A1* | 3/2016 | Gregory et al. | .. A61M 5/14248 604/150 |

FOREIGN PATENT DOCUMENTS

| WO | WO-2016053954 A1 | 4/2016 | |
|---|---|---|---|
| WO | WO 2016130679 A2 * | 8/2016 | ........ A61M 5/14248 |
| WO | WO-2016130679 A2 | 8/2016 | |
| WO | WO 2017007952 A1 * | 1/2017 | ........ A61M 5/14248 |
| WO | WO-2017007952 A1 | 1/2017 | |

OTHER PUBLICATIONS

Written Opinion for International Application PCT/US2018/017904, dated Jun. 6, 2018.
Japanese Patent Application No. 2019-544659, Notice of Rejection, dated Oct. 19, 2021.

* cited by examiner

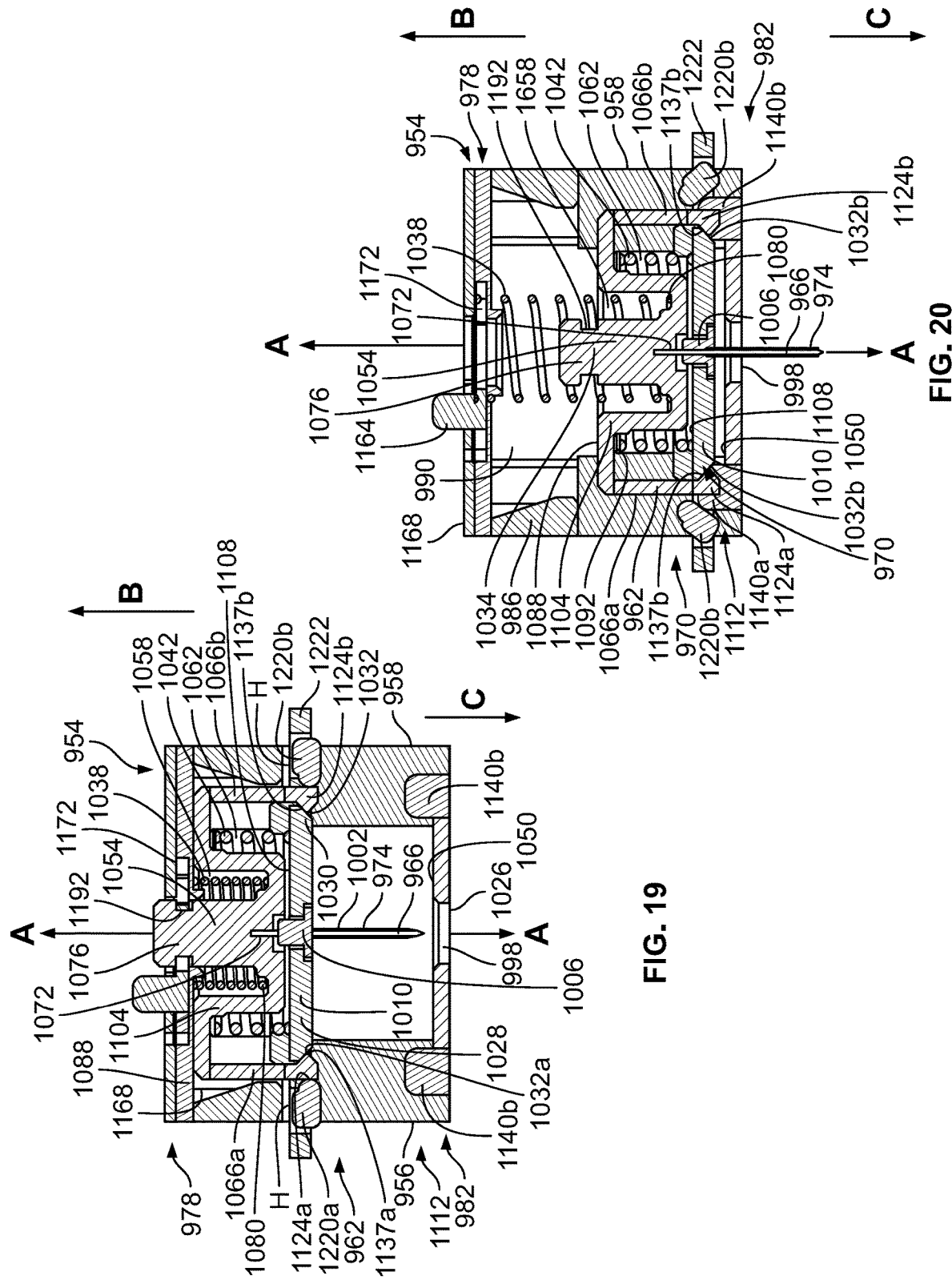

CANNULA INSERTION AND RETRACTION MECHANISMS

CROSS-REFERENCE TO RELATED APPLICATION

This is the United States national phase of International Patent Application No. PCT/US2018/17904 filed Feb. 13, 2018, which claims priority to U.S. Provisional Patent Application No. 62/460,501, filed Feb. 17, 2017, the entire contents of each of which being hereby incorporated by reference.

FIELD OF THE DISCLOSURE

The present disclosure generally relates to drug delivery devices, and more particularly, mechanisms and methods for inserting a trocar and/or cannula of a drug delivery device into a patient so that a volume of a drug stored in the drug delivery device can be delivered to the patient.

BACKGROUND

Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. For example, viscous drugs, including some biologics, can have long injection times due to the force needed to expel them from the drug delivery device. Furthermore, some drug delivery devices are configured to be attached to the patient at a doctor's office, and then later deliver the drug to the patient when the patient returns to his or her home. For these reasons and others, a rigid injection member may be left inside the patient for a substantial amount of time, which can result in patient discomfort or unease.

To address this issue, some drug delivery devices incorporate a cannula made of a flexible material for delivering the drug to the patient. Such a cannula can bend to adjust to the patient's body movements and therefore may be more comfortable than a rigid needle. However, due to its flexibility, the cannula may have difficulty penetrating the patient's skin during insertion. Therefore, an introducer needle or trocar is sometimes used to initially penetrate the skin and create a passageway for the cannula. The trocar may be subsequently retracted, leaving the cannula partially inside the patient's body.

The insertion and/or retraction movements of the trocar and/or cannula may be accomplished by incorporating an insertion mechanism disposed within the drug delivery device. Such an insertion mechanism, however, may increase the overall size, complexity, and/or cost of the drug delivery device.

The present disclosure sets forth insertion mechanisms and related methods embodying advantageous alternatives to existing insertion mechanisms and methods that may address one or more of the challenges or needs described herein, as well as provide other benefits and advantages.

SUMMARY

In accordance with a first aspect, a wearable drug delivery device may include a main housing, a container disposed in the main housing, an insertion mechanism disposed in the main housing, and a fluid pathway connector defining a sterile fluid flowpath between the container and the insertion mechanism. The insertion mechanism may include a trocar, a cannula axially aligned with the trocar and having a hollow interior, and an insertion mechanism housing having a proximal end and a distal end. Further, the insertion mechanism may include a manifold configured to fluidly connect the hollow interior of the cannula and the fluid pathway connector and a manifold guide carrying the manifold and movable relative to the insertion mechanism housing between a first position and a second position. The manifold guide may be located at the distal end of the insertion mechanism housing when in the second position. Further, a hub may carry the trocar and may be removably connected to the manifold guide. An insertion biasing member may be initially retained in an energized state between the proximal end of the insertion mechanism housing and the hub, and a retraction biasing member may be initially retained in an energized state between the hub and the manifold guide.

In accordance with a second aspect, an insertion mechanism for a drug delivery device may include a trocar, a cannula axially aligned with the trocar and including a hollow interior, and a housing having a proximal end and a distal end. The insertion mechanism may further include a manifold in fluid communication with the hollow interior of the cannula and a manifold guide carrying the manifold and movable relative to the housing between a first position and a second position, the manifold guide being located at the distal end of the housing in the second position. Further, the mechanism may include a hub carrying the trocar and removably connected to the manifold guide, an insertion biasing member initially retained in an energized state between the proximal end of the housing and the hub, and a retraction biasing member initially retained in an energized state between the hub and the manifold guide.

In accordance with a third aspect, an insertion mechanism for a drug delivery device may include a trocar, and a cannula axially aligned with the trocar and including a hollow interior. Further, the insertion mechanism may include a housing having a proximal end and a distal end, a manifold in fluid communication with the hollow interior of the cannula, and a manifold guide carrying the manifold. The manifold guide may be movable relative to the housing between a first position and a second position, where the manifold guide may be located at the distal end of the housing in the second position. A hub may carry the trocar and may be operatively connected to the manifold guide. An insertion biasing member may be initially retained in an energized state between the proximal end of the housing and the manifold guide, and a retraction biasing member may be initially retained in a non-energized state between the hub and the proximal end of the housing.

In accordance with a fourth aspect, a method may include providing a wearable drug delivery device comprising a container, a drug disposed in the container, an insertion mechanism, and a fluid pathway connector defining a sterile fluid flow path between the container and the insertion mechanism, the insertion mechanism having an insertion mechanism housing, a hub, a trocar secured to the hub, a manifold guide removably connected to the hub, a manifold carried by the manifold guide and in fluid communication with the fluid pathway, a cannula secured to the manifold, an insertion biasing member initially held between the hub and the insertion mechanism housing, and a retraction biasing member initially held between the hub and the manifold guide. The method may include disposes the wearable drug delivery device in contact with a patient's skin. Further, the method includes releasing the insertion biasing member to move the hub, the trocar, the manifold guide, the manifold, and the cannula in a distal direction so that the trocar and cannula penetrate the patient's skin. By disconnecting the hub from the manifold guide within the insertion mechanism housing, the retraction biasing member may be allowed to expand and move the trocar and the hub in a proximal direction, thereby retracting the trocar from the patient. Further, the method may include expelling the drug from the container, through the fluid pathway connector, and into the cannula for delivery to the patient.

In further accordance with any one or more of the foregoing first, second, and third aspects and method, the insertion mechanism for a drug delivery device and method may include any one or more of the following forms or method steps.

In one form, the insertion mechanism may include a disconnect member configured to disconnect the manifold guide and the hub when the manifold guide moves to the second position, thereby allowing the retraction biasing member to move the hub in a proximal direction.

In one form, the insertion mechanism may include a deformable tab initially connecting the manifold guide and the hub, the deformable tab engaging the disconnect member when the manifold guide moves to the second position to disconnect the manifold guide and the hub.

In one form, the deformable tab may be configured to slide against the disconnect member and deform by expanding outwardly relative to the manifold guide, thereby disconnecting the manifold guide and the hub.

In one form, the disconnect member may include a ramp disposed at the distal end of the insertion mechanism housing, the ramp having an inclined surface configured to engage the deformable tab and outwardly displace the deformable tab relative to the manifold guide.

In one form, the manifold guide may include a first shoulder, a second shoulder, and an aperture defined between the first and second shoulders, the deformable tab contacting the first and second shoulders when the manifold guide is connected to the hub. The disconnect member may include a distal ramp disposed at the distal end of the insertion mechanism housing and configured to separate the deformable tab from the first and second shoulders of the manifold guide, wherein the aperture of the manifold guide is sized to receive the distal ramp when the manifold guide occupies the second position.

In one form, the retraction biasing member may include a first coil spring, and the insertion biasing member including a second coil spring concentrically arranged within the first coil spring.

In one form, the insertion mechanism may include an activation member may be configured to release the insertion biasing member thereby allowing the insertion biasing member to move the manifold guide and hub in a distal direction to insert the trocar and cannula.

In one form, the drug delivery device may include a drug stored in the container.

In one form, the fluid pathway connector may include a flexible fluid conduit.

In one form, the manifold may include an internal chamber and a septum.

In one form, each of the cannula and the flexible fluid conduit may be in fluid communication with the internal chamber of the manifold during drug delivery.

In one form, each of the cannula and the flexible fluid conduit may be connected to the manifold such that each of the cannula and the flexible fluid conduit moves relative to the insertion mechanism housing when the manifold guide moves between the first position and the second position.

In one form of the insertion mechanism, the hub may be movable relative to the housing between a first hub position and a second hub position, the hub being located at the proximal end of the housing in the first hub position.

In one form of the insertion mechanism, the disconnect member may include a ramp located at the distal end of the housing, the ramp configured to engage with the deformable tab when the hub occupies the second hub position.

In one form, the disconnect member may include a ramp located at the distal end of the housing and configured to outwardly bias the deformable tab away from the manifold guide when the hub moves from the first hub position to the second hub position.

In one form, the deformable tab may include a tapered distal end configured to slide against the disconnect member and deform by expanding outwardly relative to the manifold guide, thereby disconnecting the manifold guide and the hub.

In one form, the ramp may include an inclined surface and the deformable tab may include a corresponding angled surface, the ramp configured to engage the angled surface of the deformable tab and outwardly bias the deformable tab relative to the manifold guide to disconnect the manifold guide and the hub.

In one form, the hub may include a first spring seat and a second spring seat, the insertion biasing member being held in the energized state between the proximal end of the housing and the first spring seat of the hub, the retraction biasing member being held in the energized state between the manifold guide and the second spring seat, the first spring seat being radially inward of the second spring seat.

In one form, the activation member may include a latch movable relative to the housing, the latch being configured to lockingly engage the portion of the hub prior to activation of the insertion biasing member, the latch being configured to disengage from the portion of the hub to release the insertion biasing member upon activation of the insertion biasing member.

In one form, the disconnect member may include a rotatable plate disposed at the distal end of the housing. The rotatable plate may include a slot configured to receive the deformable tab when the manifold guide occupies the second position, and the rotatable plate may be configured to rotate relative to the manifold guide and deform the deformable tab received in the slot to allow the manifold guide to disconnect from the hub.

In one form, the disconnect member includes a sliding plate disposed at the distal end of the housing. The sliding plate may be configured to displace the deformable tab away from the manifold guide when the sliding plate slides toward the manifold guide and the manifold guide occupies the second position.

In one form, the insertion mechanism may include a spring-biased retaining member initially retaining the deformable tab in connection with the manifold guide and the hub. The spring-biased retaining member may be configured to engage the disconnect member and rotate relative to the deformable tab during operation of the insertion mechanism, wherein rotation of the spring-biased retaining member allows the deformable tab to move relative to the manifold guide such that the manifold guide disconnects from the hub.

In one form, the disconnect member includes a pin disposed at the distal end of the housing and the manifold guide may be rotatable relative to the hub. The manifold guide may include an aperture with an asymmetrical cross-section, the aperture sized to receive the pin and with a bottom end offset from a top end.

In one form, the insertion mechanism may include a deformable ring initially connecting the manifold guide and the hub, the deformable ring engaging the distal end of the housing and disconnecting the manifold guide from the hub when the manifold guide occupies the second position.

In one form, the deformable ring being configured to expand radially outwardly relative to the hub, thereby disconnecting the manifold guide and the hub.

In one form, the insertion biasing member may include a coil spring and the retraction biasing member may include a disc spring at least partially arranged within the coil spring.

In one form, the retraction biasing member may be held in an energized state when the manifold occupies the second position.

In one form, the activation member may include a cam movable relative to the housing. The manifold guide may provide a deformable tab engaged with a portion of the housing prior to activation of the insertion biasing member. The cam may be configured to outwardly bias the deformable tab away from engagement with the portion of the housing to release the insertion biasing member.

In one form of the method, disconnecting the hub from the manifold guide may include engaging a deformable tab and a disconnect member, the deformable tab initially connecting the manifold guide and the hub.

In one form of the method, disconnecting the hub from the manifold guide may include sliding the hub relative to a ramp disposed within the housing when the hub moves from the first position to the second position, the ramp separating the hub from the manifold guide.

In one form of the method, engaging the deformable tab with the disconnect member may include receiving the deformable tab in a slot of a rotatable plate, and rotating the rotatable plate relative to the insertion mechanism housing to outwardly displace the deformable tab and disconnect the hub from the manifold guide.

In one form of the method, engaging the deformable tab with the disconnect member may include sliding a plate of the disconnect member relative to the insertion mechanism housing to outwardly displace the deformable tab and disconnect the hub from the manifold guide.

In one form of the method, disconnecting the hub from the manifold guide may include rotating a spring-biased retaining member from a retaining position, where the spring-biased retaining member inhibits separation of the manifold guide and the hub, to a releasing position, where the spring-biased retaining member allows the manifold guide to disconnect from the hub.

In one form of the method, disconnecting the hub from the manifold guide may include rotating the manifold guide relative to the hub while the hub moves from the first hub position to the second hub position.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

FIG. 19 illustrates a cross-sectional view of yet another embodiment of an insertion mechanism in a pre-fired configuration.

FIG. 20 illustrates the insertion mechanism of FIG. 19 in a position between the pre-fired configuration and an inserted configuration.

DETAILED DESCRIPTION

Figure 1:
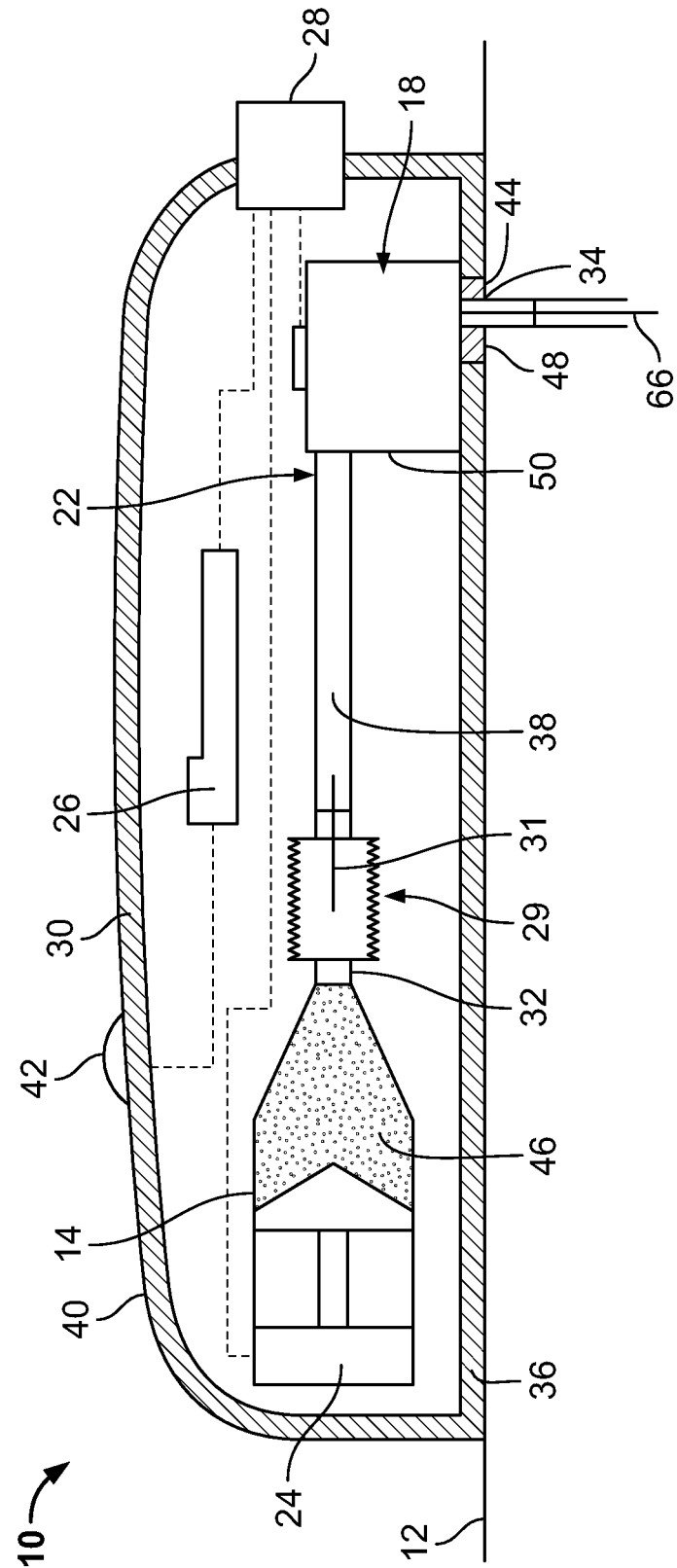
FIG. 1 is a schematic representation of one embodiment of a drug delivery device having an insertion mechanism in accordance with teachings of the present disclosure.

FIG. 1 illustrates one embodiment of a drug delivery device 10 according to the present disclosure. In at least one embodiment, the drug delivery device 10 may be configured as a wearable drug delivery device, such as an on-body injector, that may be attached to a patient's tissue 12 (e.g., the patient's skin) to administer delivery of a drug treatment. The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 may include a container 14, an insertion mechanism 18, a fluid pathway connector 22, a drive mechanism 24, and a controller 26, each of which may be disposed in a main housing 30 of the drug delivery device 10. An actuator 28 (e.g., a depressible button) may be arranged on the exterior of the main housing 30 and configured to initiate operation of the drug delivery device 10 by activating the insertion mechanism 18, the drive mechanism 24, and/or the controller 26 via mechanical and/or electrical means (shown in dotted lines in FIG. 1). The fluid pathway connector 22 defines a sterile fluid flow path 38 between the container 14 and the insertion mechanism 18. The fluid pathway connector 22 may include a container access mechanism 29 configured to insert a container needle 31 through a septum 32 associated with the container 14 to establish fluid communication between the container 14 and the sterile fluid flow path 38 in response to activation of the drug delivery device 10, for example, via the actuator 28. The main housing 30 may include a bottom wall 36 to be releasably attached (e.g., adhered with an adhesive) to the patient's skin 12, and a top wall 40 including one or more indicator lights 42 and/or a window (not illustrated) for viewing the container 14. An opening 44 may be formed in the bottom wall 36, and optionally a septum 48 may extend across the opening 44 to seal the interior of the main housing 30 prior to use. The exterior of the insertion mechanism 18 may be defined by an insertion mechanism housing 50 separate from the main housing 30.

Upon activation of the drug delivery device 10, the insertion mechanism 18 may insert a cannula 34 and/or a trocar 66 through the opening 44 and/or septum 48 and into the patient 12. Simultaneously or subsequently, the drug delivery device 10 may enable, connect, or open necessary connections to establish fluid communication between the container 14 and the fluid pathway connector 22. Next, the drive mechanism 24 may force a drug 46 stored in the container 14 through the sterile fluid flow path 38 of the fluid pathway connector 22 and into the cannula 34 for subcutaneous delivery to the patient.

FIGS. 2-7 illustrate an insertion mechanism 54 corresponding to one embodiment of the insertion mechanism 18 illustrated in FIG. 1. The insertion mechanism 54 may be incorporated in a drug delivery device such as the drug delivery device 10 depicted in FIG. 1. The insertion mechanism 54 includes an insertion mechanism housing 58, a trocar assembly 62 having a trocar 66, a cannula assembly 70 possessing a cannula 74 axially aligned with the trocar 66, and an activation member 76. In some embodiments, the trocar 66 may have a sharpened or beveled distal tip so that the trocar 66 is capable of piercing the patient's skin 12 and introducing the cannula 74 inside the patient. The trocar 66 may also be referred to as an introducer needle, and does not include a hollow center. To facilitate this introducing functionality, the trocar 66 may be made of a more rigid material than the cannula 74. In some embodiments, the trocar 66 may be made of metal, whereas the cannula 74 may be made of plastic. Moreover, the relative flexibility of the cannula 74 may render the cannula 74 suitable for being left inside the patient for several minutes, hours, or days without substantial discomfort to the patient. In other embodiments, the trocar 66 may be replaced with a hollow needle disposed within the hollow cannula 74.

The insertion mechanism housing 58, also referred herein as the housing, includes a proximal end 78, a distal end 82, and a walled enclosure 86 or casing defining an interior space 90. In the initial pre-fired configuration shown in FIG. 2, the trocar and cannula assemblies 62 and 70 are enclosed within the interior space 90 of the housing 58. The trocar and cannula assemblies 62 and 70 are movable relative to the housing 58 along a longitudinal axis A of the housing 58 and each assembly moves between a first position (FIG. 2) and a second position (FIG. 3).

Figure 2:
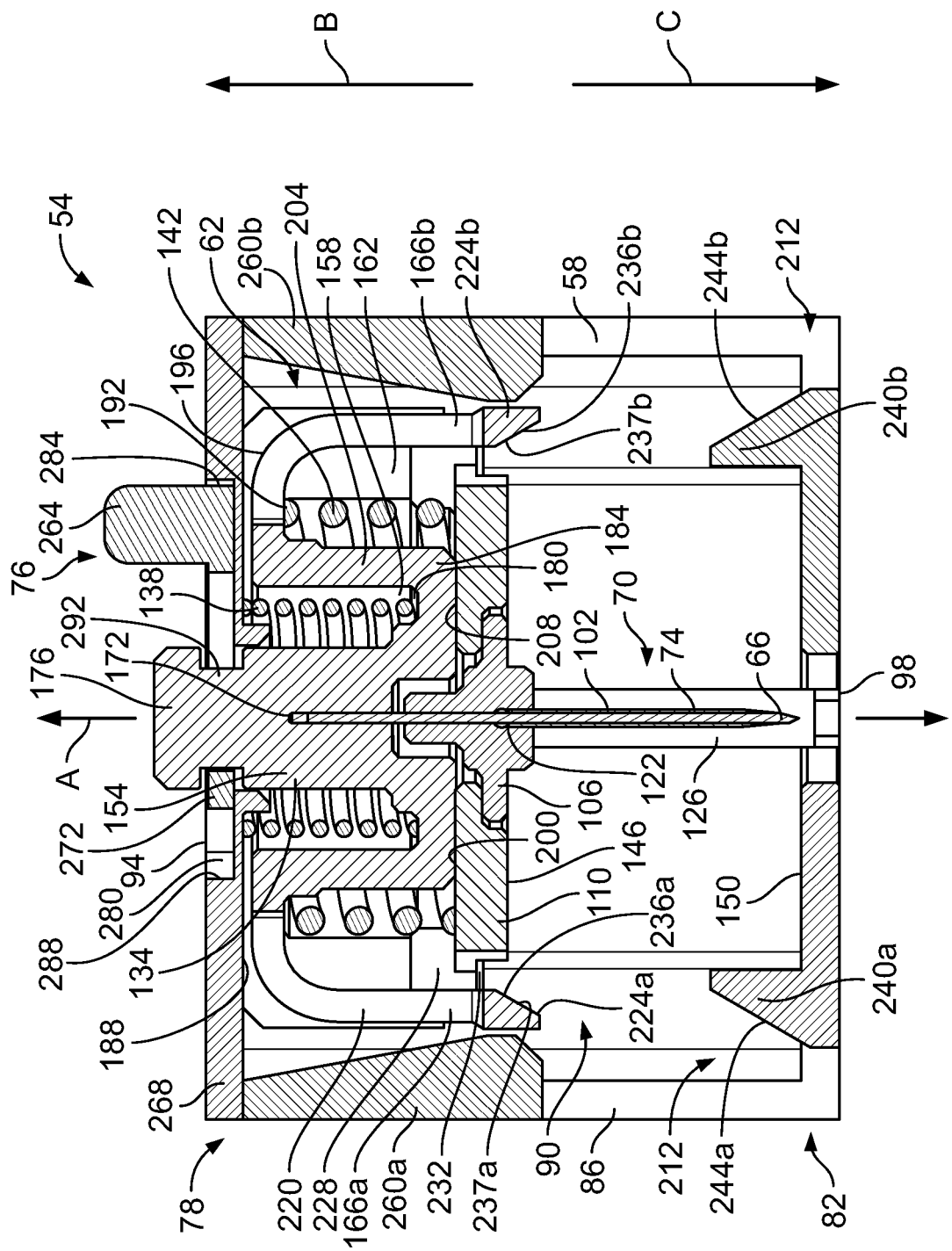
FIG. 2 illustrates a cross-sectional view of one embodiment of an insertion mechanism in a pre-fired configuration assembled in accordance with teachings of the present disclosure.

As shown in FIG. 2 when the insertion mechanism 54 is in the pre-fired configuration, a portion of the trocar assembly 62 extends through an aperture 94 formed in the proximal end 78 of the housing 58. Both trocar and cannula assemblies 62 and 70 occupy a first position in the pre-fired configuration. In FIG. 3, the insertion mechanism 54 is arranged in an inserted configuration and the trocar and cannula assemblies 62 and 70 are each located near the distal end 82 of the housing 58. Upon release of the activation member 76, the trocar and cannula assemblies 62 and 70 move from the first position to the second position shown in FIG. 3. An opening 98 formed in the distal end 82 of the housing 58 permits insertion of the cannula 74 and the trocar 66 into a patient to establish a fluid pathway for drug delivery. After insertion of the cannula 74, the trocar assembly 62 moves to the first position to pull the trocar 66 back inside the housing 58 while the cannula assembly 70 remains in the second position near the distal end 82 of the housing 58. This configuration of the insertion mechanism 54, also referred to herein as the retracted configuration, is depicted in FIG. 4. Here, it is shown that the trocar assembly 62 is positioned near the proximal end 78 of the housing 58 and the cannula assembly 70 remains in the second position. As a result, the trocar 66 is fully retracted from the patient and the distal end of the cannula 74 remains inside the patient for delivering the drug.

Figure 3:
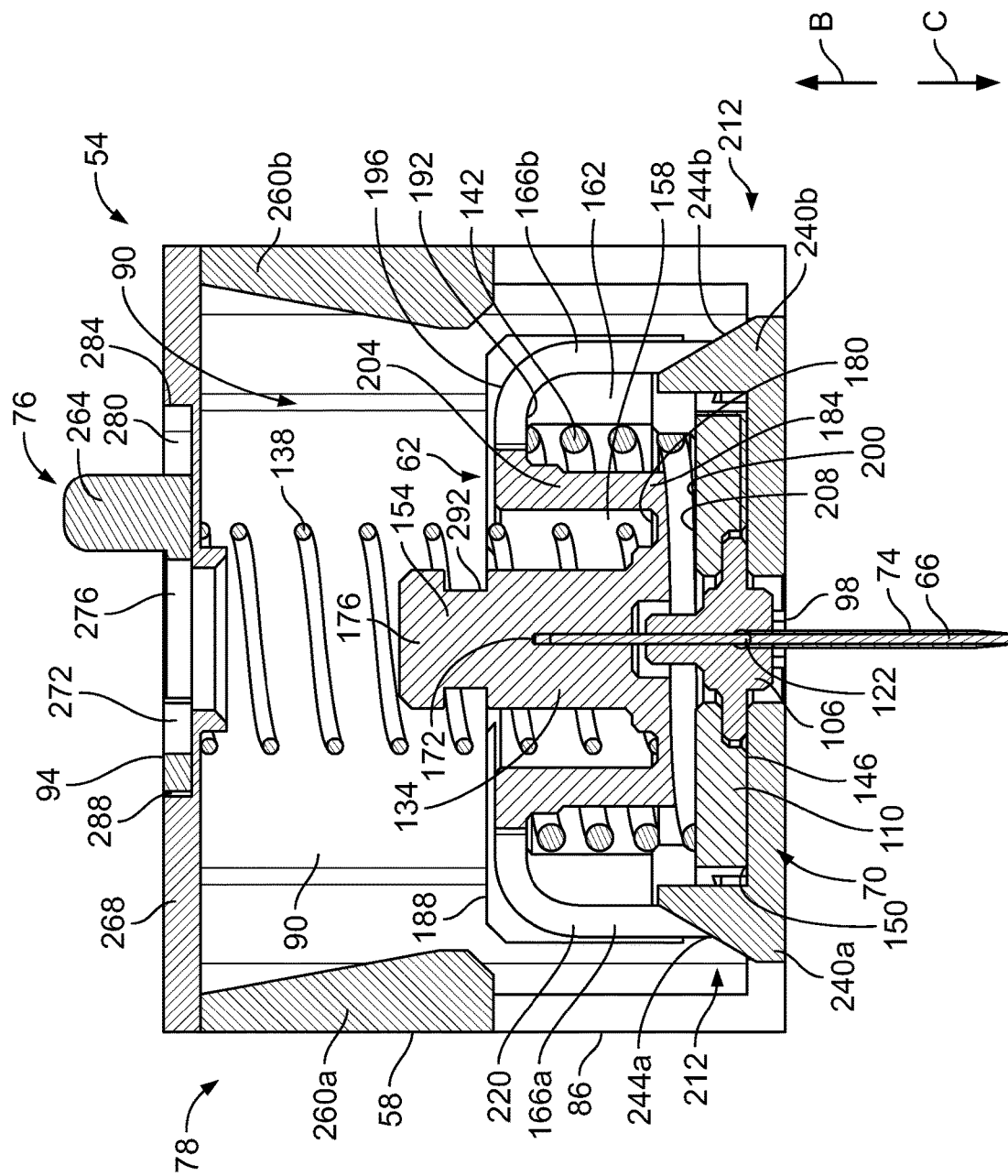
FIG. 3 illustrates the insertion mechanism of FIG. 2 in an inserted configuration.
Figure 4:
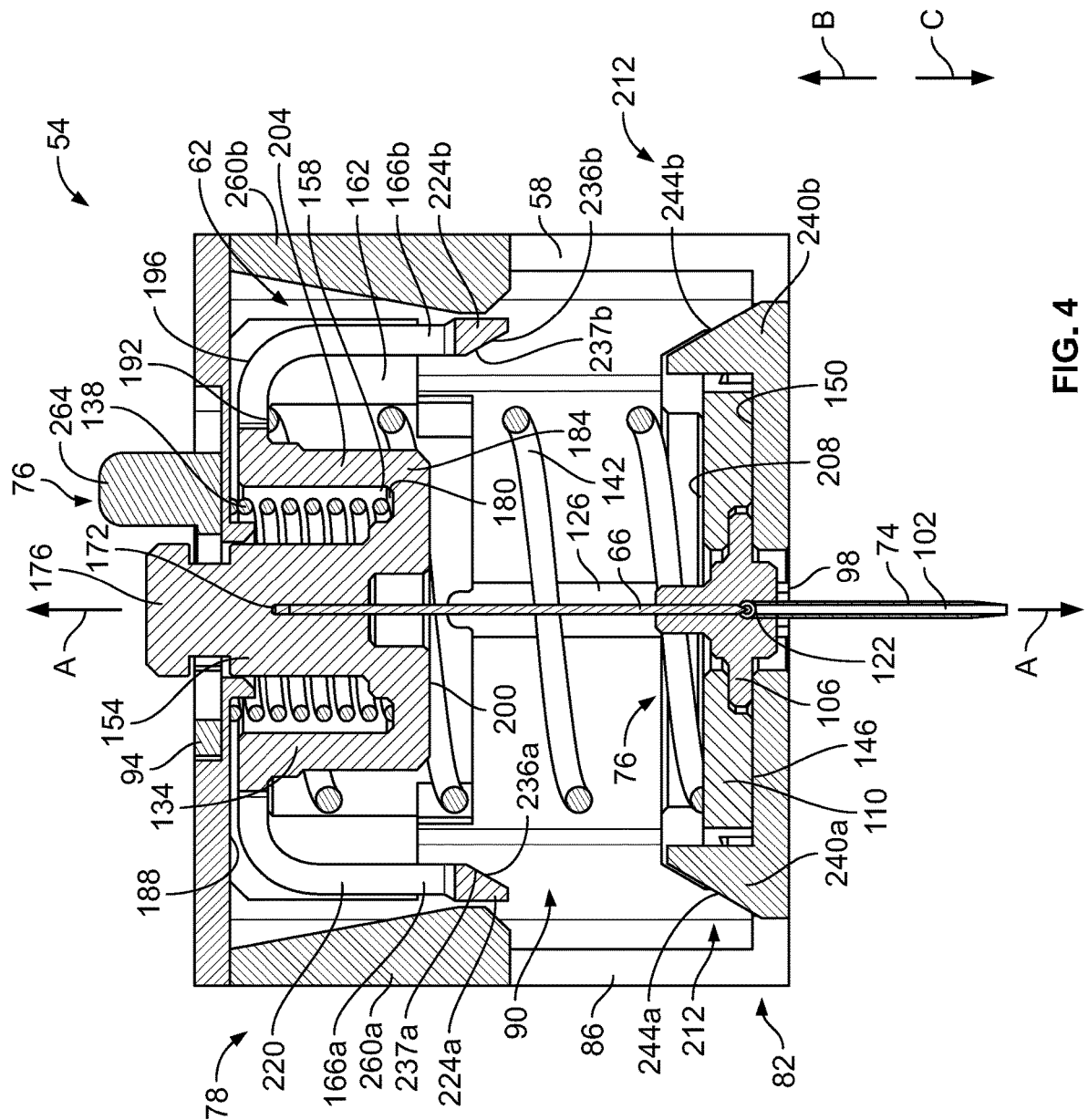
FIG. 4 illustrates the insertion mechanism of FIGS. 2 and 3 in the retracted configuration.
Figure 5:
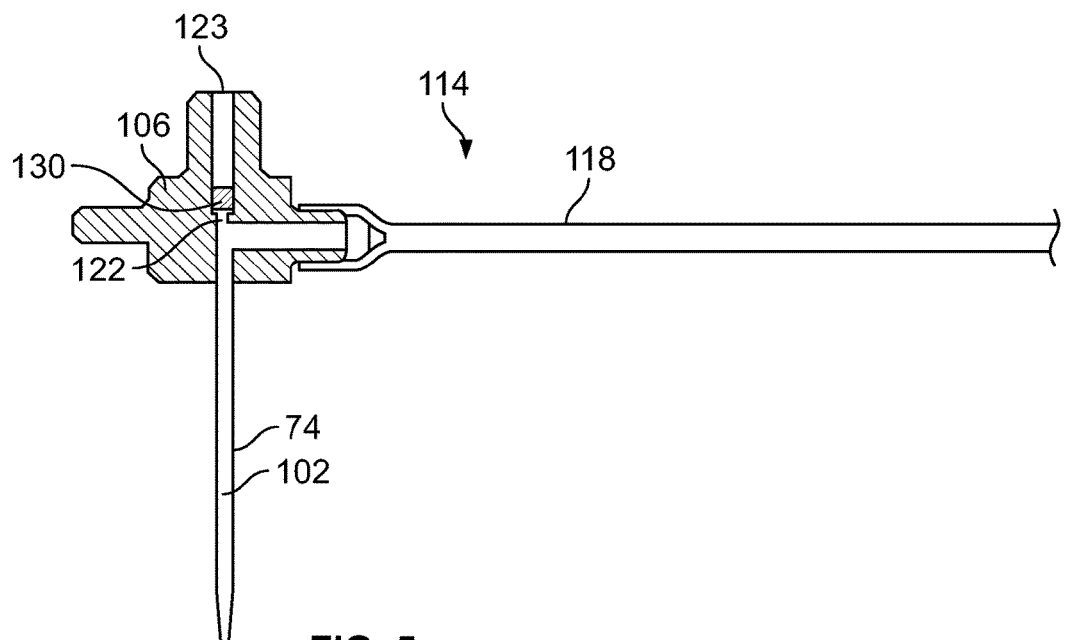
FIG. 5 illustrates a cross-sectional view of a manifold, cannula, and a fluid pathway connector of the insertion mechanism of FIGS. 2-5.

As shown in FIGS. 2-4, the cannula assembly 70 includes the cannula 74 having a hollow interior 102, a manifold 106 carrying the cannula 74, and a manifold guide 110 carrying the manifold 106. The manifold guide 110, the manifold 106, and the cannula 74 are movable relative to the insertion mechanism housing 58 between the first position shown in FIG. 2 and the second position shown in FIG. 3. The manifold guide 110 and manifold 106 are located at the distal end 82 of the housing 5 when arranged in the second position. The manifold 106 is configured to fluidly connect the hollow interior 102 of the cannula 74 and a fluid pathway connector 114, which extends into the page in FIGS. 2-4 and is depicted in FIG. 5. The fluid pathway connector 114 and the cannula 74 are connected to the manifold 106 such that the cannula 74 and the fluid pathway connector 114 can move relative to the housing 58 when the insertion mechanism 54 is activated. The fluid pathway connector 114 includes a flexible fluid conduit 118 in fluid communication with an internal chamber 122 of the manifold 106. The flexible fluid conduit 118 may define a portion, or the entirety, of the sterile fluid flow path 38 depicted in FIG. 1. As shown in FIGS. 2 and 4, a vertical channel or opening 126 formed in the casing 86 of the housing 58 permits the fluid pathway connector 114 and flexible fluid conduit 118 to move relative to the housing 58 when the manifold guide 110 and manifold 106 move between first and second positions.

In FIG. 5, the manifold 106 includes a septum 130 disposed in the internal chamber 122 of the manifold 106. The trocar 66 is disposed through the septum 130 when the insertion mechanism 54 is both in the pre-fired and inserted configurations. As the trocar assembly 62 returns to the first position, the trocar 66 moves in a proximal direction B (shown in FIGS. 2-4) relative to the housing 58, thereby passing through the internal chamber 122, the septum 130, and an opening 123 in a proximal end of the manifold 106. The septum 130 seals the opening 123 closed so that fluid cannot escape through the opening 123 during drug delivery. In some embodiments, the trocar 66 may fully retract from the internal chamber 112 when the cannula assembly 70 is arranged in the second position so that the trocar 66 is isolated from the sterile fluid flow path during drug delivery.

The trocar assembly 62 includes the trocar 66, a hub 134 carrying the trocar 66, an insertion biasing member 138, and a retraction biasing member 142. The hub 134 is removably connected to the manifold guide 110 and becomes disconnected from the manifold guide 110 to permit the trocar assembly 62 to retract to the second position, as shown in FIG. 4, when the insertion mechanism 54 is in a retracted configuration. The trocar 66 moves together with the hub 134 as the hub 134 moves from a first hub position shown in FIGS. 2 and 4 to a second hub position shown in FIG. 3. The cannula 74, which is carried by the manifold 106, moves with the manifold guide 110 from the first position shown in FIG. 2 to the second position shown in FIG. 3, and remains in the second position when the insertion mechanism 54 is in the retracted configuration as seen in FIG. 4. The trocar 66 is disposed within the hollow interior 102 of the cannula 74 in the pre-fired configuration in FIG. 2 and when the hub 134 moves from the first hub position to the second hub position shown in FIG. 3. When the insertion mechanism 54 is arranged in the inserted configuration, the trocar 66 and the cannula 74 extend through the opening 98 in the distal end 82 of the housing 58. The trocar 66 is configured to pierce the skin 12 of a patient and create a passageway for the cannula 74. A bottom surface 146 of the manifold guide 110 may directly contact an inside surface 150 of the distal end 82 of the housing 58 when the manifold guide 110 is in the second position, as depicted in FIGS. 3 and 4. The bottom surface 146 of the manifold guide 110 abuts the inside surface 150 of the distal end 82 of the housing 58, thereby limiting the distance the trocar 66 and the cannula 74 can travel through the opening 98 of the housing 58 and into the patient. When the trocar 66 reaches an end of its stroke, it may retract immediately to minimize discomfort for the patient. As shown in FIG. 4, the hub 134 is disconnected from the manifold guide 110 and the trocar 66 is retracted back into the interior space 90 of the housing 58. The cannula 74 remains in an extended position, corresponding to the second position, during drug delivery.

The hub 134 includes a central member 154, a first concentric groove 158 surrounding the central member 154, a second concentric groove 162 spaced outwardly from the first concentric groove 158, and a deformable tab 166a and 166b defining the outermost portion of the hub 134 relative to the longitudinal axis A. As illustrated in FIGS. 2-4, the hub 134 includes first and second deformable tabs 166a and 166b disposed radially outwardly of the central member 154 of the hub 134. The central member 154 includes a bore 172 that receives the trocar 66 and a proximal portion 176 that is configured to engage the activation member 76. The first concentric groove 158 is adjacent to the central member 154 and extends axially along the longitudinal axis A from a first spring seat 180 at a distal end 184 of the hub 134 through a top surface 188 of the hub 134. The second concentric groove 162 extends from a second spring seat 192 at a proximal end 196 of the hub 134 through a bottom surface 200 of the hub 134. The first groove 158 and the second groove 162 are radially separated by an inner hub wall 204, and the second groove 162 is located radially between the inner hub wall 204 and first and second deformable tabs 166a and 166b. So configured, the second groove 162 has a diameter larger than a diameter of the first groove 158. As shown in FIG. 2, the insertion biasing member 138 is initially retained in an energized state, which in the present embodiment corresponds to a compressed configuration of the insertion biasing member 138, between the proximal end 78 of the housing 58 and the hub 134. More particularly, the insertion biasing member 138 is compressed between the first spring seat 180 of the hub 134 and a top portion 268 of the housing 58 in its energized state. Similarly, the retraction biasing member 142 is initially retained in an energized state, which in the present embodiment corresponds to a compressed configuration of the retraction biasing member 142, between the hub 134 and the manifold guide 110. More particularly, the retraction biasing member 142 is compressed between the second spring seat 192 of the hub 134 and a top surface 208 of the manifold guide 110 in its energized state.

In the illustrated embodiment, the retraction biasing member 142 is defined by a first coil spring, and the insertion biasing member 138 is defined by a second coil spring concentrically arranged within the first coil spring. In this version, the retraction biasing member 142 has a diameter larger than a diameter of the insertion biasing member 138. In alternative embodiments, the coil spring defining the retraction biasing member 142 may be concentrically arranged within the coil spring defining the insertion biasing member 138. In still further alternative embodiments, the insertion biasing member 138 and/or the retraction biasing member 142 may be defined by a pressurized gas mechanism, an electric motor, an elastic membrane, a torsion spring, a leaf spring, and/or any other suitable mechanism for storing and releasing energy for moving the components associated with insertion and retraction. Returning to the illustrated embodiment, the insertion biasing member 138 and the retraction biasing member 142 are arranged such that upon release of the activation member 76, the insertion biasing member 138 expands axially in a distal direction C, thereby driving the hub 134 from the first hub position to the second hub position. In FIG. 3, the insertion biasing member 138 is in an expanded configuration, or de-energized state, and the hub 134 is arranged in the second hub position. The manifold guide 110 is driven from the first position to the second position concurrently with the movement of the hub 134 as the hub 134 moves from the first hub position to the second hub position. Once the hub 134 and manifold guide 110 reach their respective second positions located at the distal end 82 of the housing 58 (as shown in FIG. 3), a disconnect member 212 disconnects the manifold guide 110 and the hub 134, allowing the retraction biasing member 142 to expand axially in the proximal direction B to retract the trocar 66. FIG. 4 illustrates the retraction biasing member 142 in an expanded state or partially de-energized state, biasing the hub 134 away from the distal end 82 of the housing 58 and retaining the hub 134 in the first hub position. As shown in FIG. 4, the manifold guide 110 is disconnected from the hub 134 and the trocar 66 is isolated from the internal chamber 122 of the manifold 106.

Figure 6:
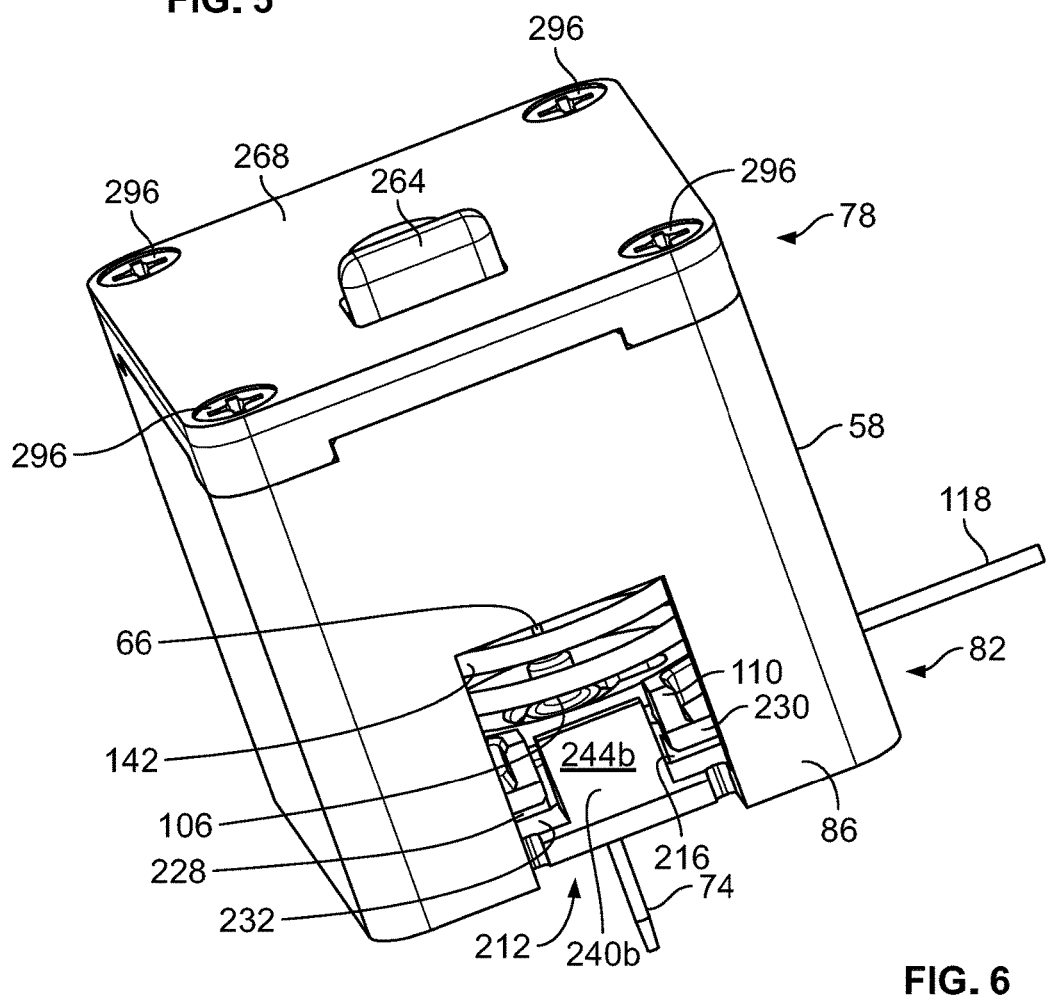
FIG. 6 illustrates a perspective view of one embodiment of the insertion mechanism in the retracted configuration.
Figure 7:
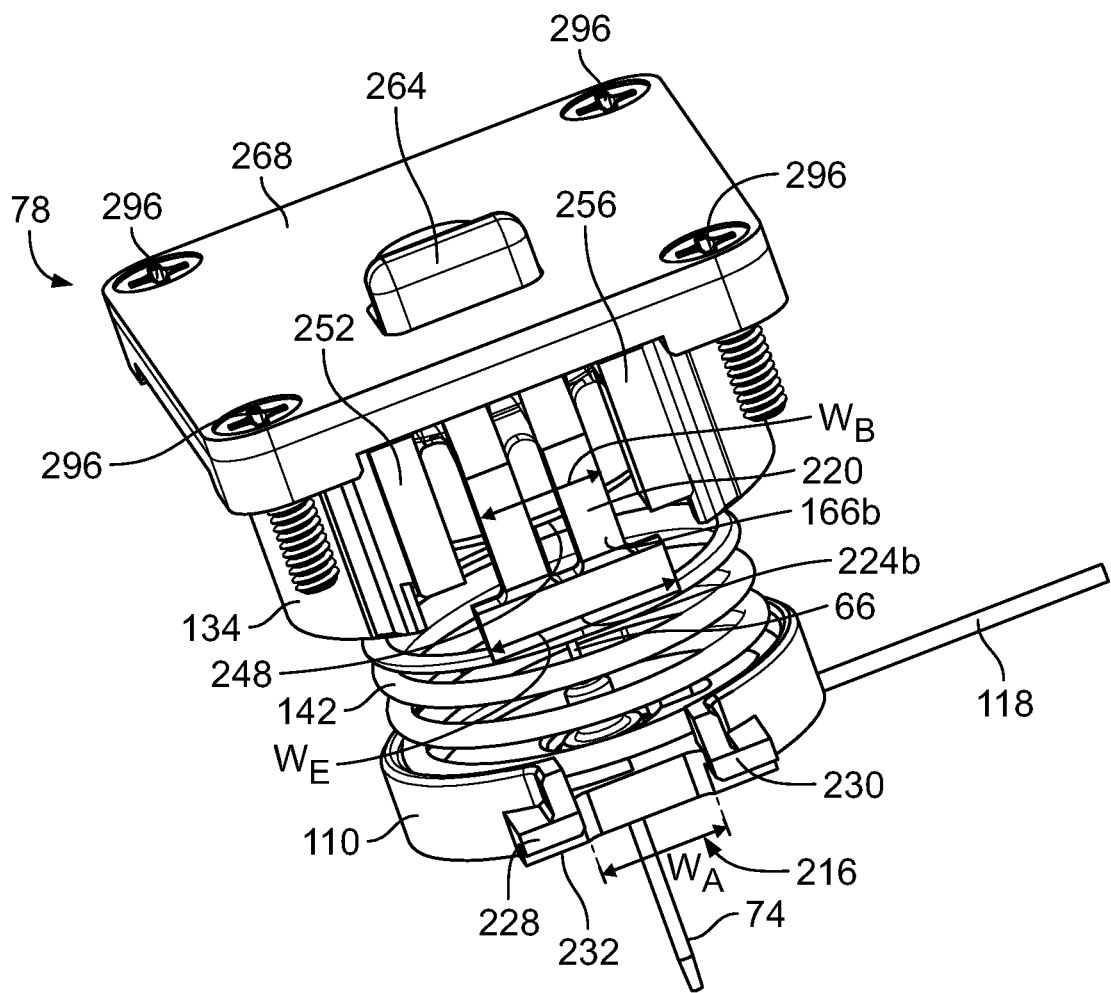
FIG. 7 illustrates the insertion mechanism of FIG. 6 with a portion of the housing hidden.
Figure 8:
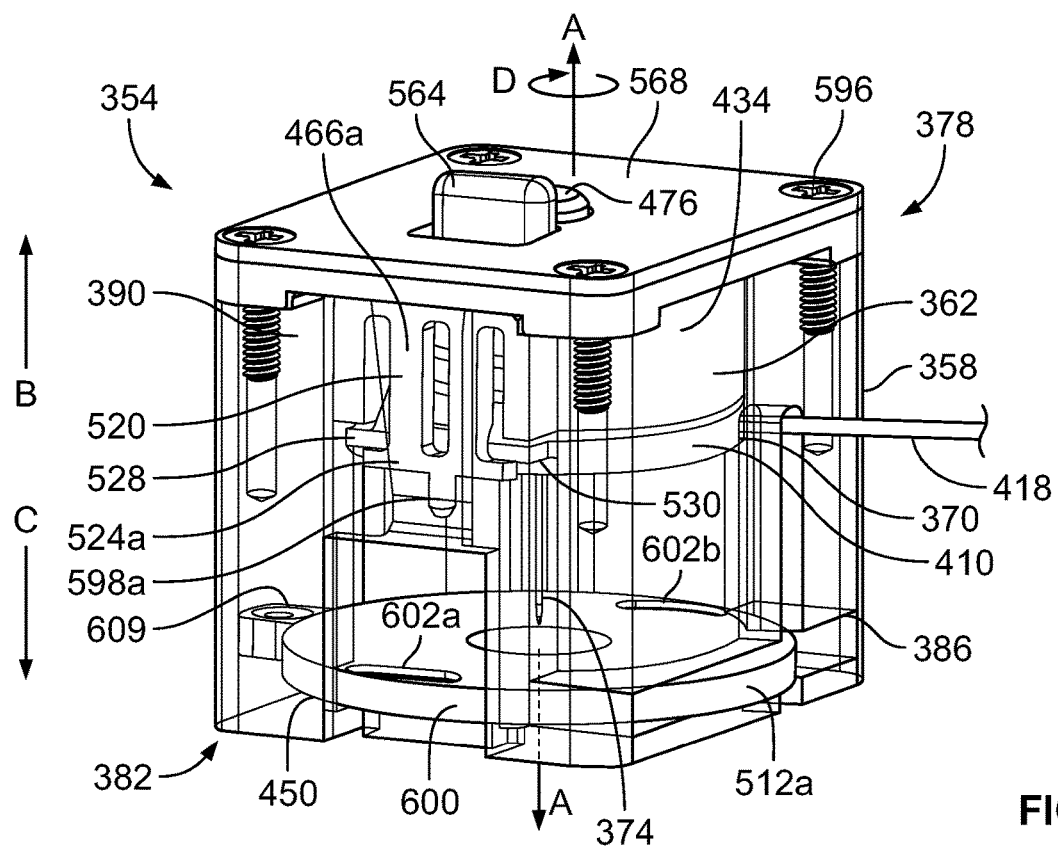
FIG. 8 illustrates a perspective view of a different embodiment of an insertion mechanism in a pre-fired configuration, the insertion mechanism having a rotatable plate.

The hub 134 and the manifold guide 110, which are removably connected, move together as a unit as the insertion mechanism 54 transitions from the pre-fired configuration to the inserted configuration. Joint movement of the hub 134 and the manifold guide 110 is possible until the hub 134 and manifold guide 110 are disconnected. In the illustrated embodiment, the first and second deformable tabs 166a and 166b removably connect the manifold guide 110 and the hub 134, and are configured to engage the disconnect member 212 when the manifold guide 110 occupies the second position. Each of the first and second deformable tabs 166a and 166b is configured to engage, or interlock with, a corresponding first or second receiving aperture 216 formed in the manifold guide 110. Each deformable tab 166a and 166b includes a flexible body 220 with a wide distal end 224a, 224b. The first and second receiving apertures 216 may be aligned with the first and second deformable tabs 166a and 166b. As illustrated in FIGS. 6 and 7, each of the receiving apertures 216 is defined by a first shoulder 228 and a second shoulder 230 of the manifold guide 110. Furthermore, each of the receiving apertures 216 includes a width $W_A$ that is equal to or greater than a width $W_B$ of the flexible body 220 of the deformable tab 166a, 166b and is narrower than a width $W_E$ of the wide distal end 224b of the deformable tab 166b. When the manifold guide 110 and the hub 134 are connected, the distal end 224b of the deformable tab 166b contacts a bottom surface 232 of the first and second shoulders 228, 230 of the manifold guide 110, limiting the upward vertical displacement of the hub 134 relative to the location of the manifold guide 110.

Referring back to FIGS. 2 and 4, the distal ends 224a and 224b of the deformable tabs 166a and 166b each include a tapered end 236a or 236b having an inclined surface 237a or 237b configured to engage with the disconnect member 212. Each of the inclined surfaces 237a and 237b may be non-parallel to the longitudinal axis A and form an angle of less than 90 degrees relative to the longitudinal axis A. The distal ends 224a and 224b of the deformable tabs 166a and 166b may be configured to slide against the disconnect member 212 causing the flexible body 220 to deform by expanding outwardly relative to the manifold guide 110. As the flexible body 220 flexes outwardly away from the shoulders 228 and 230 of the manifold guide 110, the manifold guide 110 disconnects from the hub 134. As shown in FIGS. 2-4 and 6, the disconnect member 212 may include ramps 240a and 240b disposed on opposite sides of the distal end 82 of the housing 58. The ramps 240a and 240b may possess, respectively, inclined surfaces 244a and 244b. The inclined surfaces 244a and 244b may be configured to engage, respectively, the inclined surfaces 237a and 237b of the deformable tabs 166a and 166b. The inclined surfaces 244a and 244b of the ramps 240a and 240b may be non-parallel to the longitudinal axis A and form an angle of less than 90 degrees relative the longitudinal axis A. In some embodiments, the inclined surface 237a and the inclined surface 244a may form the same, or substantially the same, angle relative to the longitudinal axis A. Similarly, the inclined surface 237b and the inclined surface 244b may form the same, or substantially the same, angle relative to the longitudinal axis A. Accordingly, flush engagement of the inclined surfaces 237a and 237b with their corresponding inclined surfaces 244a and 244b may be possible. The inclined or angled surfaces 244a and 244b of the ramps 240a and 240b may displace the deformable tab 166a and 166b in the outward radial direction away from the longitudinal axis A as the hub 134 moves from the first hub position to the second hub position. As a result, the inclined surface 244a and 244b may disconnect the hub 134 and the manifold guide 110 by separating the deformable tabs 166a and 166b from the manifold guide 110. The inclined surfaces 244a and 244b of the ramps 240a and 240b outwardly push the deformable tabs 166a and 166b as they slide in the distal direction C down the angled ramps 240a and 240b. The wide distal ends 224a and 224b move away from the bottom surface 232 of the first and second shoulders 228, 230, allowing the hub 134 to move independently from the manifold guide 110. As illustrated in FIG. 6, the ramps 240a and 240b of the disconnect member 212, which may be attached to or integrally formed with the housing 58, may be sized to fit within the aperture 216 of the manifold guide 110. As such, the ramps 240a and 240b displace the deformable tabs 166a and 166b when the manifold guide 110 occupies the second position.

FIG. 7 illustrates the deformable tab 166b having a channel 248 formed in the flexible body 220. The channel 248 may allow the flexible body 220 to deform such that the deformable tab 166b can expand outwardly without fracturing. Once the deformable tab 166b flexes outwardly and disconnects from the first and second shoulders 228 and 230 of the manifold guide 110, the deformable tab 166b may return to its original shape as illustrated in FIG. 4. The deformable tab 166a may have a similar construction and operation as the deformable tab 166b.

In the present embodiment, the deformable tabs 166a and 166b are integrally formed with the hub 134; however, in other embodiments, the deformable tabs 166a and 166b may be integrally formed with the manifold guide 110. The insertion mechanism 54 may include connecting members to removably connect the manifold guide 110 and the hub 134, such as, for example, an adhesive or a female and male key and key slot configuration. Additionally, the disconnect member 212 may be disposed at a different location within the housing 58. In some embodiments, the disconnect member 212 may be a component separate from the housing 58. The disconnect member 212 may include an engaging surface that is configured to separate or unlock the connecting members of the hub 134 and the manifold guide 110.

Referring to FIGS. 2-4, the housing 58 may include ramps 260a and 260b located at the proximal end 78 of the housing 58. The ramps 260a and 260b each may inwardly protrude from the casing 86 of the housing 58 to keep the deformable tabs 166a and 166b from splaying outwardly. Accordingly, the ramps 260a and 260b may help secure the connection between the deformable tabs 166a and 166b and the manifold guide 110 when the insertion mechanism 54 occupies the pre-fired configuration. When the hub 134 moves from the first hub position to the second hub position, the deformable tabs 166a and 166b may slide past their corresponding ramps 260a and 260b and subsequently slightly expand outwardly. The deformable tabs 166a and 166b may slightly expand outwardly to better engage with their corresponding inclined surfaces 244a and 244b of the ramps 240a and 240b disposed at the distal end 82 of the housing 58. When the hub 134 moves from the second hub position to the first hub position in the proximal direction B, the deformable tabs 166a and 166b may flex inwardly as they contact their corresponding ramps 260a and 260b.

The activation member 76 is configured to release the insertion biasing member 138 to permit the insertion biasing member 138 to drive the manifold guide 110 and the hub 134 in the distal direction C. As shown in FIGS. 2-4, the activation member 76 may be movable relative to the housing 58 and configured to initially engage the proximal portion 176 of the hub 134 to inhibit or prevent the insertion biasing member 138 from expanding. The activation member 76 may be configured to disengage from the proximal portion 176 of the hub 134 to release the insertion biasing member 138. Referring to FIG. 3, the activation member 76 may include a latch tab 264 extending from the top portion 268 of the housing 58, a latch body 272, and an aperture 276 formed in the latch body 272. The latch body 272 is disposed within a depression 280 formed in the top portion 268 of the housing 58 and is configured to slide between a first end 284 of the depression 280 and a second end 288 of the depression 280. In the pre-fired configuration shown in FIG. 2, the latch tab 264 is located at the first end 284 of the depression 280 and the latch body 272 contacts a groove 292 formed in the central member 154 of the hub 134. When the activation member 76 is released/fired, the latch body 272 moves away from the groove 292 and moves out of contact with the proximal portion 176 of the hub 134. The latch body 272 is configured to slide to the second end 288 of the depression 280 to permit the proximal portion 176 of the hub 134 to slide through the aperture 276 of the latch body 272. In FIG. 3, the latch body 272 is arranged at the second end 288 of the depression 280 and disengaged from the groove 292 of central member 154 of the hub 134. In some embodiments, the activation member 76 of the insertion mechanism 54 may be mechanically connected to actuator 28 such that manual movement of the actuator 28 by a patient or healthcare provider may activate the insertion mechanism 54. In other embodiments, movement of activation member 76 may be accomplished by electromechanical means operated by the controller 26 in response to movement of the actuator 28 by the patient or healthcare provider.

FIG. 7 illustrates the insertion mechanism 54 without the casing 86 of the housing 58 and in the retracted configuration. The retraction biasing member 142 biases the hub 134 and the insertion biasing member 138 to keep the hub 134 in the first hub position. The manifold guide 110 may include an aperture to allow the fluid connector 118 to remain in fluid communication with the manifold 106 as the manifold guide 110 moves between the first and second positions. The retraction biasing member 142 is disposed between the second spring seat 192 of the hub 134 and the manifold guide 110. The proximal portion 176 of the hub 134 extends through the aperture 94 of the top portion 268 of the housing 58 and through the aperture 276. In the retracted configuration, the proximal portion 176 of the hub 134 is in not engaged with the latch body 272 of the activation member 76 and may be reset or reconfigured to the pre-fired configuration before a second activation or deployment of the trocar assembly 62. The top portion 268 located at the proximal end 78 of the housing 58 may be fastened to the casing 86 of the housing 58 by a plurality of fasteners 296.

Described below is one embodiment of a method of operating a drug delivery device, such as the drug delivery device illustrated in FIG. 1, incorporating the insertion mechanism 54 shown in FIGS. 2-7. The method may begin with providing a patient or a healthcare provider (e.g., a caregiver, nurse, doctor, etc.) with the wearable drug delivery device 10. Next, the patient or healthcare provider may dispose the bottom wall 36 of the drug delivery device 10 in contact with the patient's skin 12 to adhere or otherwise temporarily attach the bottom wall 36 of the drug delivery device 10 to the patient's skin 12. To activate the insertion mechanism 54, the patient or healthcare provider may depress the actuator 28, which in turn may displace the activation member 76 such that the activation member 76 disengages or releases the hub 134. As a result, the insertion biasing member 138 may be allowed to expand in the distal direction C along the longitudinal axis A of the insertion mechanism housing 58. Such expansion drives the hub 134, the trocar 66, the manifold guide 110, and the cannula 74 from the first position to the second position, thereby causing the trocar 66 to penetrate the patient's skin 12 and introduce the cannula 74 inside the patient.

Subsequently, the hub 134 may be disconnected from the manifold guide 110 to allow the retraction biasing member 142 to expand in the proximal direction B along the longitudinal axis A. Such expansion drives retraction of the trocar 66 and the hub 134 from the second position to the first position while retaining the manifold guide 110, the manifold 106, and the cannula 74 in the second position. Accordingly, the trocar 66 may be removed from the patient while the distal end of the cannula 74 is left inside the patient. Subsequent to, or concurrently with, insertion of the cannula 74, the method may include: (a) activating the container access mechanism 29 to insert the container needle 31 through the septum 32 to establish fluid communication between the container 14 and the sterile fluid flow path 38 of the fluid connector 22; and (b) activating the drive mechanism 24 to expel the drug 46 from the container 14 through the fluid pathway connector 22, and into the cannula 74 for delivery to the patient. In another example shown in FIGS. 28 and 29, the trocar 66 may be replaced with a hollow needle 67 that is directly connected to the fluid pathway connector 22. In this case, the insertion mechanism 54 may not include a manifold 106 for fluid connection to the container 14. Instead, a fluid path 119 is directly connected to a barbed end 73 of the hollow needle 67, which is configured to dispense the drug 46 into the cannula 74. In operation, a cannula guide 107, which may be similar to the manifold 106, carries the cannula 74 to the second position with the hub 134 for drug delivery, and remains in the second position when the hub 134 returns to the initial hub position. At this point, the hollow needle 67 may fluidly connect the cannula 74 to the fluid pathway connector 22 via the fluid path 119 and the drug 46 may be expelled through the hollow needle 67, through the cannula 74, and into the patient. A seal 71, such as an O-ring, is disposed around an outer diameter of the hollow needle 67 in the cannula guide 107 to provide a sealed pathway 125 for fluid delivery. The cannula guide 107 may be removably connected to the hub 134, like the manifold guide 110, or the cannula guide 107 may be removably connected to the hub 134 by another mechanism. In some embodiments, activating the insertion mechanism 54, the container access mechanism 29, and/or the drive mechanism 24 may be accomplished through a single depression of the actuator 28.

In FIGS. 8-13, an insertion mechanism 354 is illustrated in accordance with another embodiment of the present disclosure. The insertion mechanism 354 is similar to the insertion mechanism 54 described above, except for the manner in which a manifold guide 410 is connected and disconnected to a hub 434. Elements of the insertion mechanism 354 in FIGS. 8-13 which are similar to the elements of the insertion mechanism 54 are designated by the same reference numeral, incremented by 300. A description of many of these elements is abbreviated or even eliminated in the interest of brevity. Further, the insertion mechanism 354 may be incorporated into a drug delivery device such as the drug delivery device 10 depicted in FIG. 1.

Figure 10:
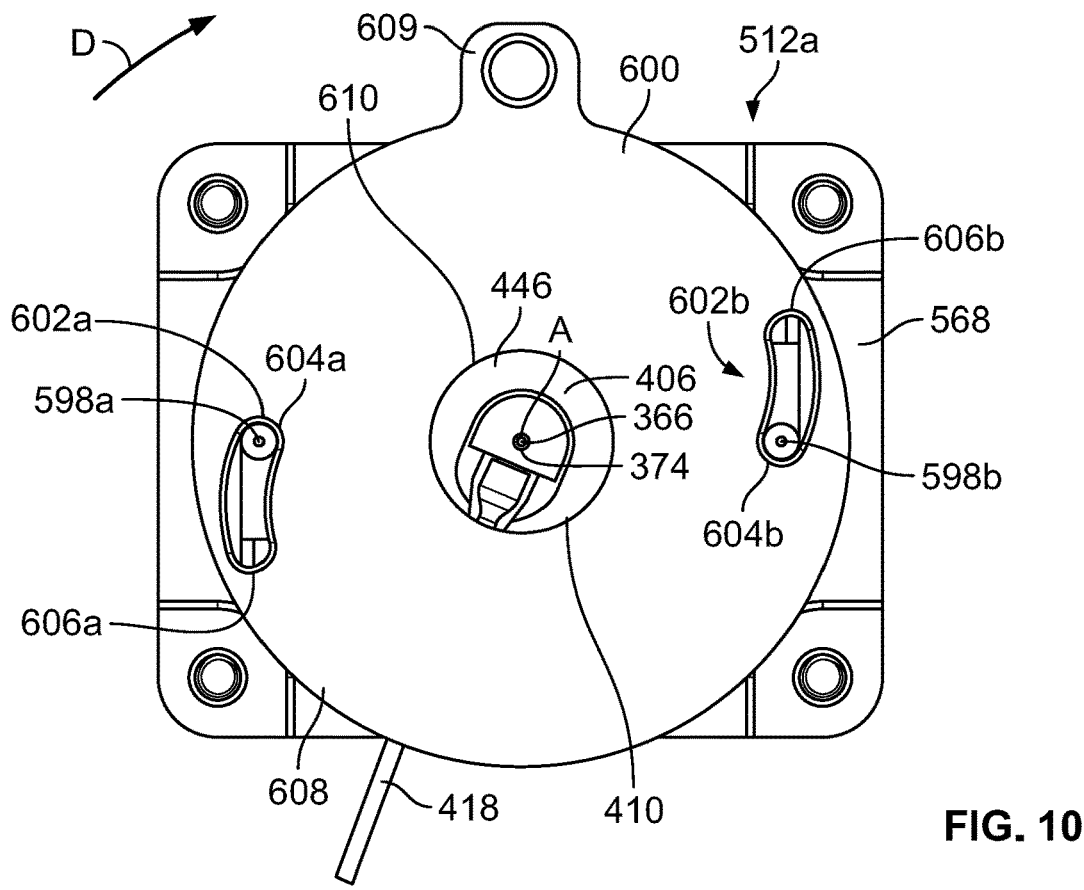
FIG. 10 illustrates a bottom view of the rotatable plate of the insertion mechanism of FIGS. 8 and 9 where the rotatable plate is in a first position.
Figure 11:
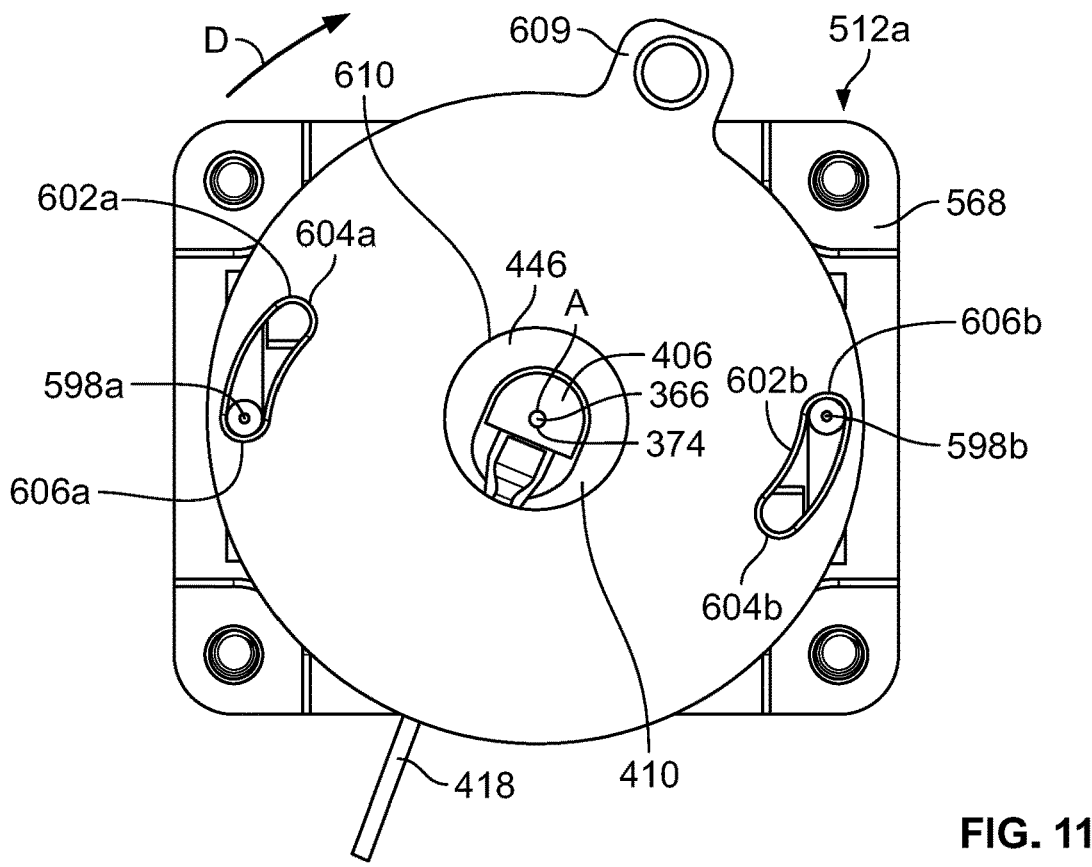
FIG. 11 illustrates the rotatable plate of FIG. 10 in a second position.
Figure 12:
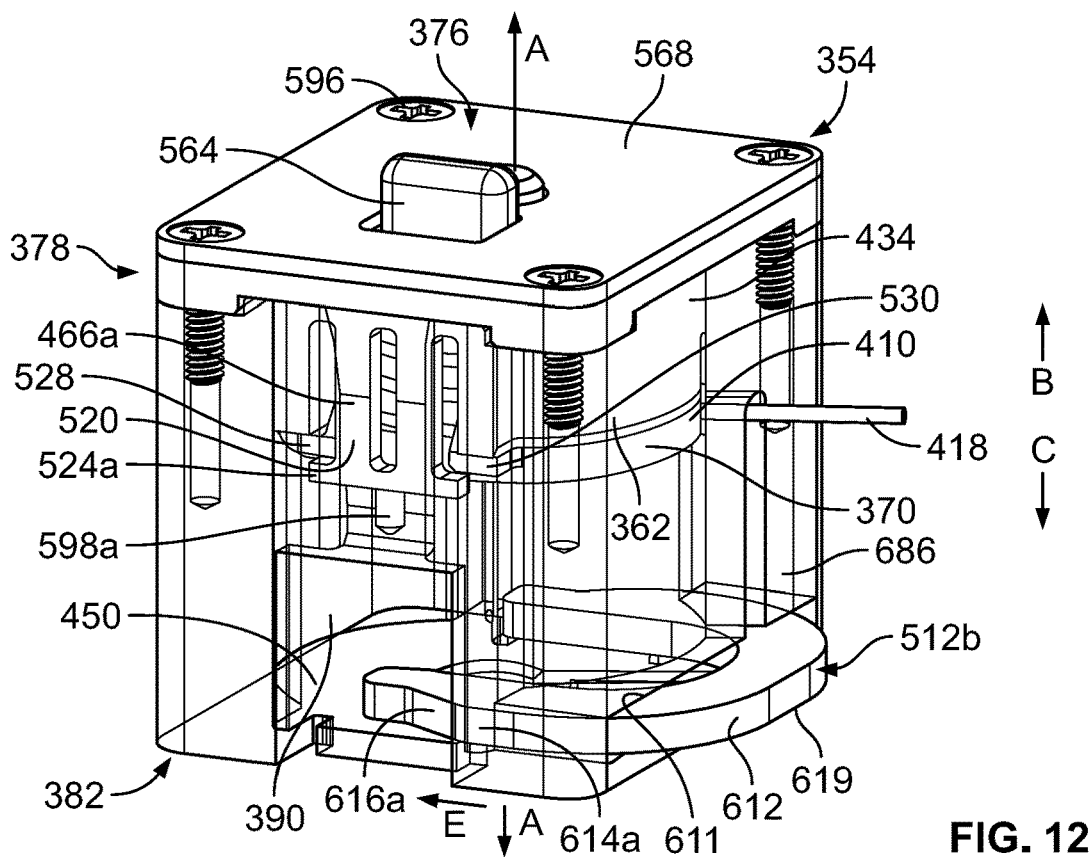
FIG. 12 illustrates a different embodiment of an insertion mechanism in a pre-fired configuration, the insertion mechanism having a sliding plate in a non-engagement position.
Figure 13:
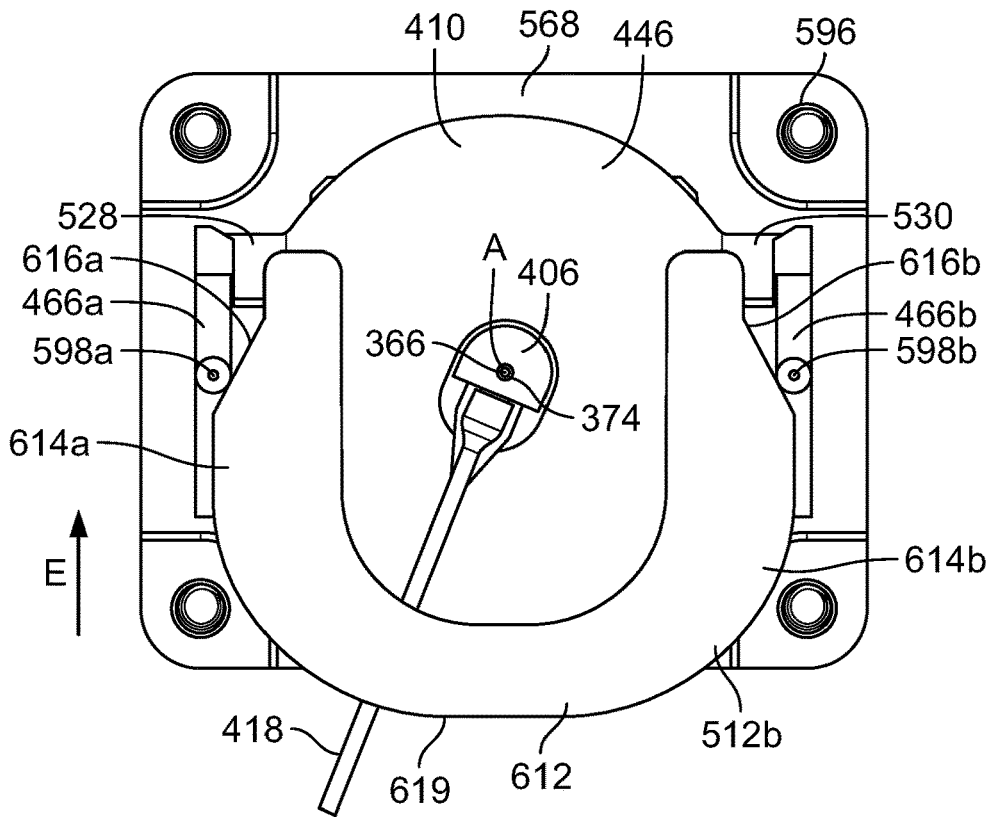
FIG. 13 illustrates a bottom view of the sliding plate of the insertion mechanism of FIG. 12 where the sliding plate is in an engagement position.
Figure 14:
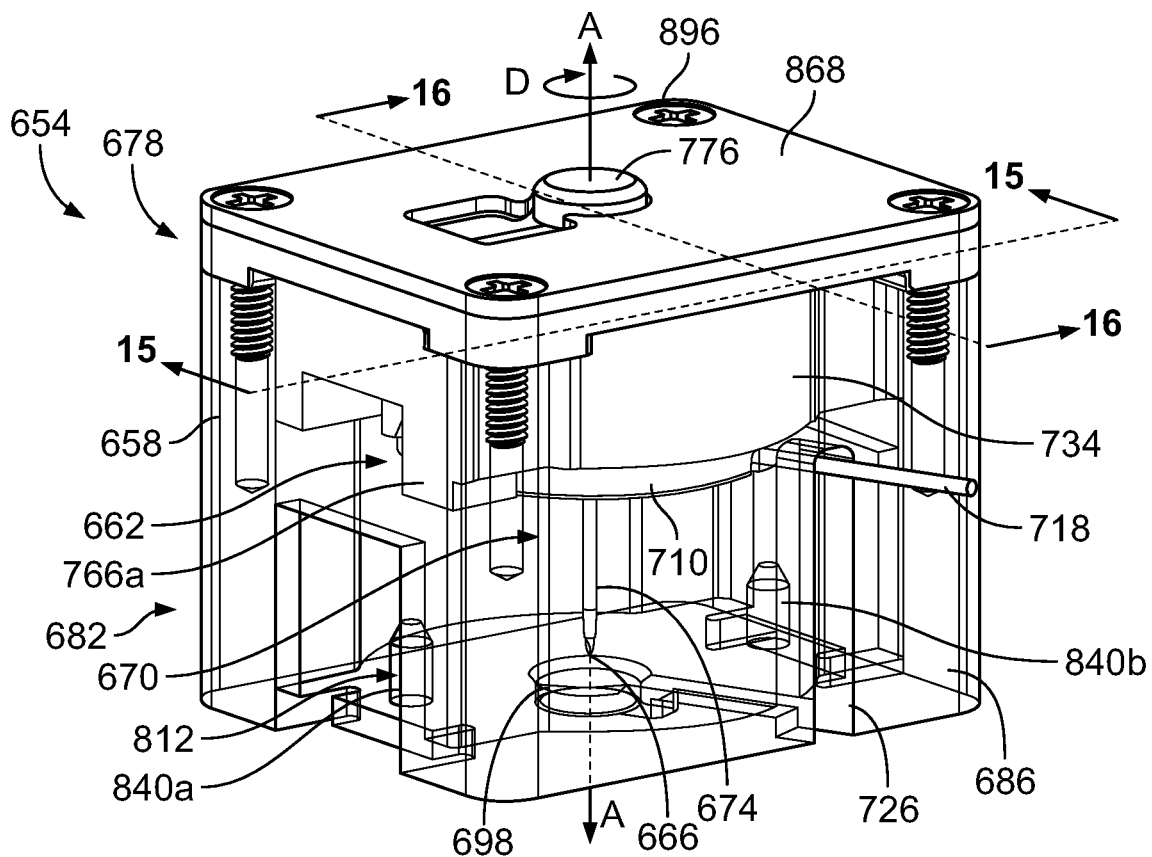
FIG. 14 illustrates a perspective view of yet another embodiment of an insertion mechanism in a pre-fired configuration.

Turning to FIGS. 8-13, the insertion mechanism 354 may include either the disconnect member 512a depicted in FIGS. 8-11 or the disconnect member 512b shown in FIGS. 12 and 13. Other configurations of the disconnect member are also possible. In the illustrated embodiments, the housing 358 may not include ramps located at the distal end 382 of the housing 358 to disconnect the manifold guide 410 and the hub 434. In the embodiment illustrated in FIGS. 8-11, the disconnect member 512a includes a rotatable plate 600 disposed at the distal end 382 of the housing 358 and is configured to rotate in direction D about the longitudinal axis A once the cannula and trocar assemblies 362 and 370 are in the inserted configuration. The rotatable plate 600 includes slots 602a and 602b corresponding to the number of deformable tabs 466a and 466b where each slot 602a and 602b is aligned to the corresponding deformable tab 466a and 466b. Each slot 602a and 602b has a first end 604a and 604b inwardly disposed relative to a second end 606a and 606b, which is disposed closer to an outer perimeter 608 of the rotatable plate 600. Each deformable tab 466a and 466b of the hub 434 includes a pin 598a and a pin 598b extending downward from the distal end 524a and 524b of the deformable tab 466a and 466b. In the pre-fired configuration shown in FIG. 8, the pins 598a and 598b are aligned with the first ends 604a and 604b of the slots 602a and 602b. In the inserted configuration shown in FIGS. 9 and 10, the manifold guide 410 occupies the second position and the pins 598a and 598b are disposed within the slots 602a and 602b at the first ends 604a and 604b.

To disconnect the manifold guide 410 and the hub 434, the rotatable plate 600 is rotated in direction D about the longitudinal axis A from a first position shown in FIG. 10 to a second position shown in FIG. 11. The plate 600 rotates relative to the manifold guide 410 and deforms the deformable tabs 466a and 466b received in the slots 602a and 602b to cause the manifold guide 410 and the hub 434 to disconnect. During rotation, the deformable tabs 466a and 466b are pushed outwardly relative to the manifold guide 410 toward the outer perimeter 608 of the rotatable plate 600 as each pin 598a and 598b slides along their respective slot 602a and 602b from the first end 604a and 604b to the second end 606a and 606b. The rotatable plate 600 effectively pushes the deformable tabs 466a and 466b via the pins 598a and 598b away from the first and second shoulders 528 and 530 of the manifold guide 410 to disconnect the manifold guide 410 and hub 434. Once the manifold guide 410 and the hub 434 disconnect, the retraction biasing member 442 may then expand in the proximal direction B to retract the trocar assembly 362 into the retracted configuration.

Figure 9:
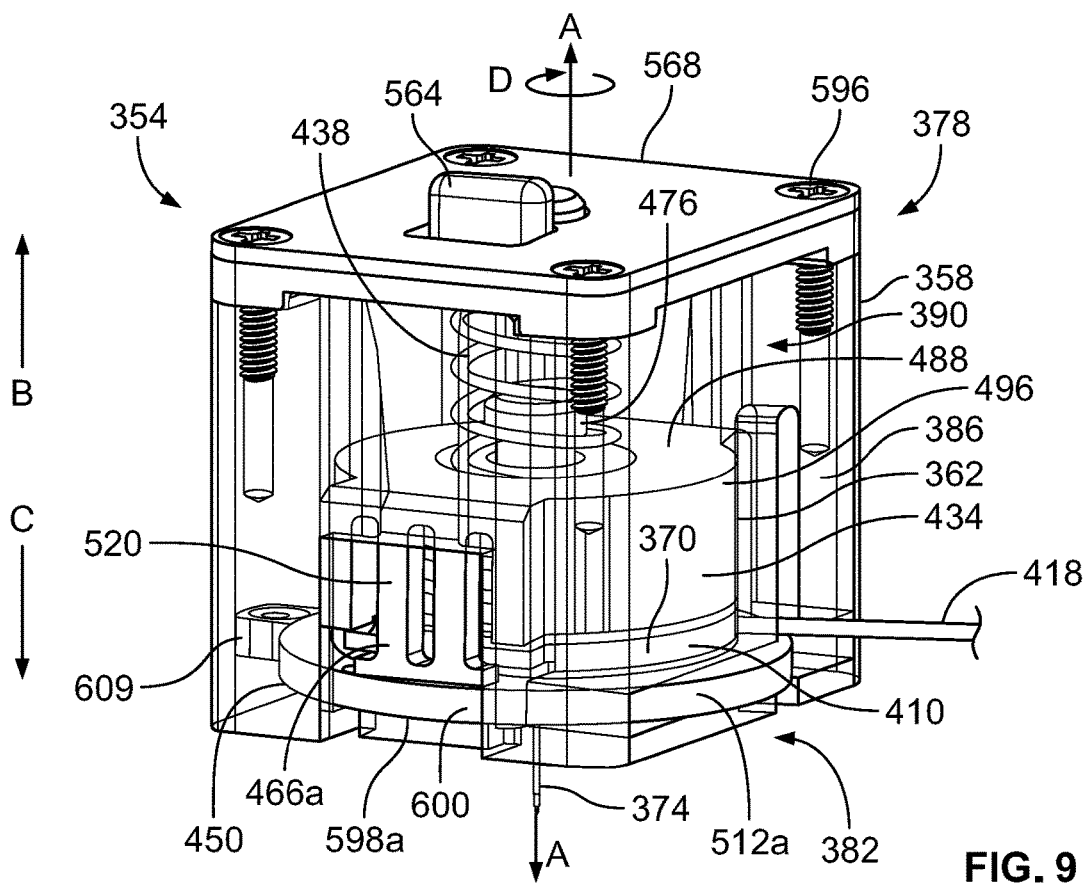
FIG. 9 illustrates the insertion mechanism of FIG. 8 in an inserted configuration.

The rotatable plate 600 may be activated by rotating the plate 600 once the trocar and cannula assemblies 362 and 370 occupy the inserted configuration shown in FIGS. 9 and 10. In the inserted configuration, the trocar 366 and cannula 374 are disposed through a central aperture 610 formed in the rotatable plate 600 and through the opening in the distal end 382 of the housing 358. To retract the trocar assembly 362, the rotatable plate 600 may be rotated in the D direction via a tab 609 disposed outside of the enclosed portion 390 of the housing 358. As the plate rotates 600 from the first position to the second position, which can be seen by a change in position of the tab 609 in FIGS. 11 and 12, the slots 602a and 602b push out the deformable tabs 466a and 466b and disconnect the manifold guide 410 and the hub 434. The rotatable plate 600 may be activated or triggered to rotate concurrently with or immediately after the cannula 374 and trocar 366 are inserted/disposed through distal end 382 of the housing 358. In another embodiment, the rotatable plate 600 may not be automatically triggered, and instead may be independently triggered to separate the insertion and retraction actions of the insertion mechanism 354. The tab 609 of the rotatable plate 600 may be coupled to a second actuator accessible from the exterior of the main housing 30 of the drug delivery device 10 of FIG. 1. The second actuator may be a depressible button or linear activation mechanism that may be activated by a patient or healthcare provider. In another embodiment, the tab 609 is coupled to another linkage system within the device 10 so that the retraction of the trocar assembly 362 and the rotation of the rotatable plate 600 is triggered independently from insertion. In another example, similar to the examples illustrated in FIGS. 28 and 29, the trocar 366 may be replaced with a hollow needle that is directly connected to the fluid pathway connector 22. In this case, the insertion mechanism 354 may not include a manifold 406 for fluid connection to the container 14. Instead, a fluid path is directly connected to the hollow needle, which is configured to dispense the drug 46 into the cannula 374. In operation, a cannula guide (e.g. a cannula guide 107 in FIGS. 28 and 29) arranged similarly to the manifold 406 and manifold guide 410 carries the cannula 374 to the second position with the hub 434 for drug delivery, and remains in the second position when the hub 434 returns to the initial hub position. At this point, the hollow needle may fluidly connect the cannula 374 to the fluid pathway connector 22 and the drug 46 may be expelled through the hollow needle, through the cannula 374, and into the patient. A seal, such as an O-ring, is disposed around an outer diameter of the hollow needle in the cannula guide to provide a sealed pathway for fluid delivery from the hollow needle to the cannula. Dispensing the drug through the hollow needle may be automatically or manually activated.

In the alternative embodiment shown in FIGS. 12, 13, 26, and 27, the disconnect member 512b is disposed at the distal end 382 of the housing 358 and includes a sliding plate 612 configured to slide towards the longitudinal axis A to engage the deformable tabs 466a and 466b and disconnect the manifold guide 410 and the hub 434. The sliding plate 612 is U-shaped with tapered arms 614a and 614b that are configured to displace the deformable tabs 466a and 466b when the sliding plate 612 slides into an engagement position shown in FIG. 13 at the same time or soon after the manifold guide 410 occupies the second position. So configured, when the manifold guide 410 occupies the second position, the sliding plate 612 may be driven into the enclosed portion 390 of the housing 358 toward the manifold guide 410. The pins 598a and 598b contact angled ends 616a and 616b of the arms 614a and 614b when the hub 434 occupies the second hub position, and the deformable tabs 466a and 466b are pushed outwardly away from the longitudinal axis A while the tapered arms 614a and 614b slide in direction E. As the sliding plate 612 slides into an engagement position, the angled ends 616a and 616b displace the pins 598a and 598b away from engagement with the shoulders 528 and 530 of the manifold guide 410. A rectangular opening 611 is formed in the distal end 382 of the housing 358 to permit the sliding plate 612 to move between a non-engagement position, shown in FIGS. 12, 26, and 27, to the engagement shown in FIG. 13. The sliding plate 612 may be pushed into the engagement position so that the sliding plate 612 engages the deformable tabs 466a and 466b before or after the trocar and cannula assemblies 362 and 370 occupy the inserted configuration. The insertion mechanism 354 may be configured to automatically retract when the sliding plate 612 is pushed into the engagement position and right before drug delivery. In another embodiment, the sliding plate 612 may be pushed into the engagement position at a time after the trocar and cannula assemblies 362 and 370 occupy the inserted configuration to provide a delayed retraction.

Figure 26:
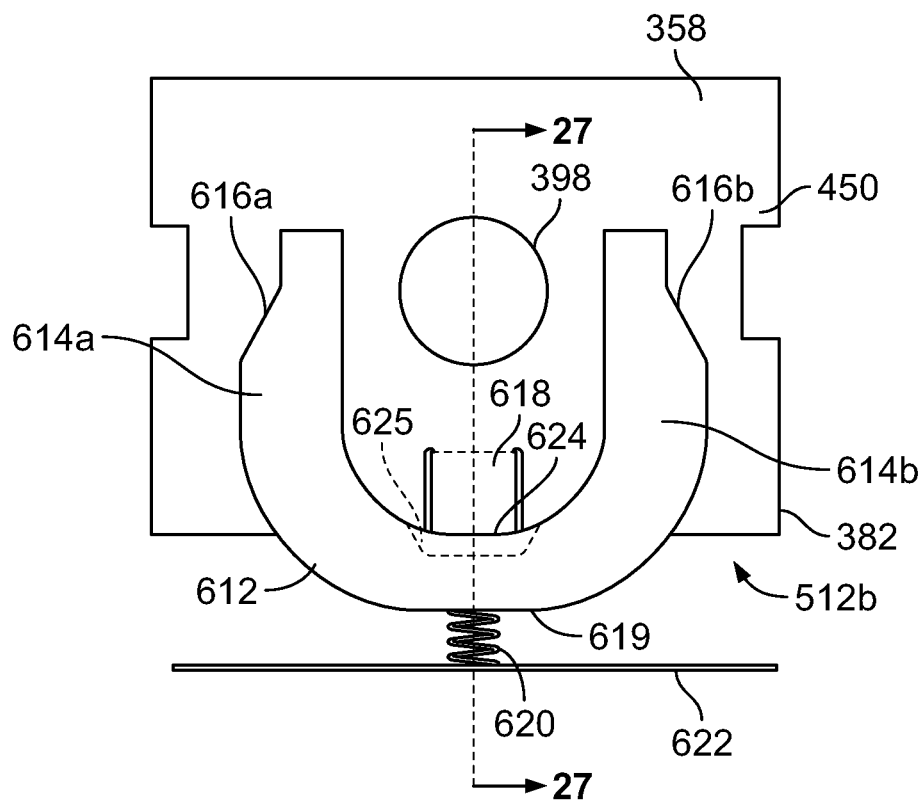
FIG. 26 illustrates a partial top view of the sliding plate of the insertion mechanism of FIGS. 12 and 13 in the pre-fired configuration.
Figure 27:
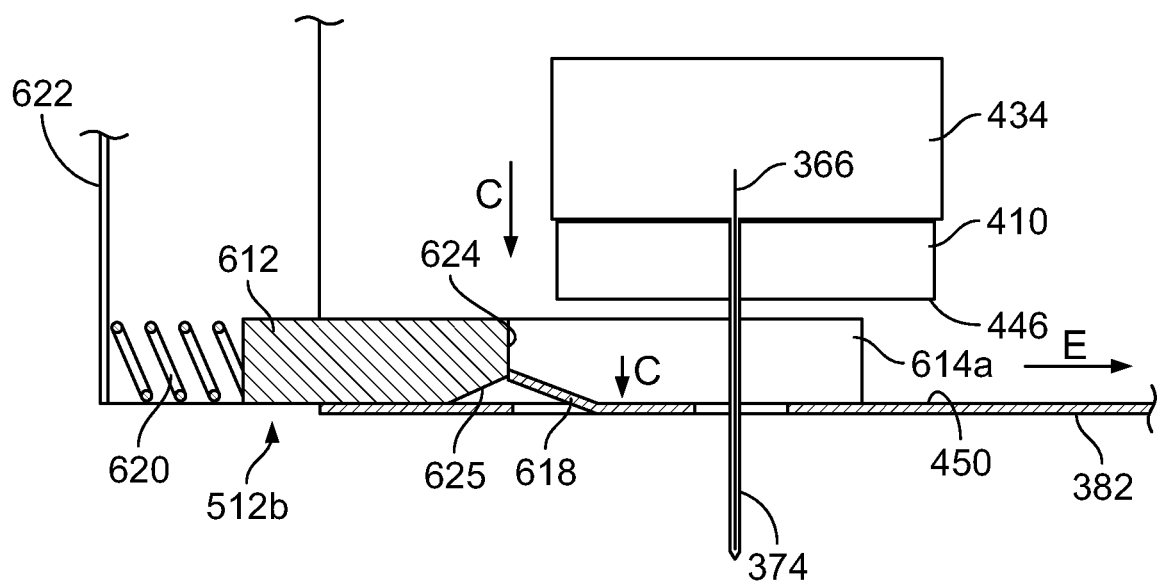
FIG. 27 illustrates a partial cross-sectional side view of the sliding plate and insertion mechanism of FIG. 26.

FIGS. 26 and 27 illustrate the sliding plate 612 held in the non-engagement position between a locking tab 618 of the housing 358 and a loaded spring 620. When the locking tab 618 is deformable and moves away from the sliding plate 612, the loaded spring 620 drives the sliding plate 612 into the engagement position. The loaded spring 620 is disposed outside of the housing 358 between an interior wall 622 of the drug delivery device 10 and a back portion 619 of the sliding plate 612. The interior wall 622 may be the wall 30 of the drug delivery device 10 or another wall, barrier, or rigid structure disposed within the housing 30 and proximally located to the insertion mechanism housing 358. The locking tab 618 extends into the interior space 390 from the bottom surface 450 of the housing 358 and engages a middle portion 624 of the sliding plate 612. The loaded spring 620 is released when the locking tab 618 is pushed out of engagement with the middle portion 624 when the manifold guide 410 moves to the second position. Specifically, the bottom surface 446 of the manifold guide 410 contacts the locking tab 618 and pushes the locking tab 618 in the distal direction C as the manifold guide 410 moves to the second position. The locking tab 618 moves in the C direction, sliding past an angled surface 625 formed in the middle portion 624 of the sliding plate 612, and out of engagement with the middle portion 624. Concurrently, or subsequently, the loaded spring 620 expands in the direction E to drive the sliding plate 612 into the engagement configuration. In the illustrated example, the locking tab 618 is molded to the bottom surface 450 of the housing 358. In another embodiment, the sliding plate 612 may be held against the loaded spring 620 by another means that is displaced when the manifold guide 410 occupies the second manifold position. In yet another embodiment, the sliding plate 612 may be biased or otherwise driven to the engagement position by another mechanism that is triggered by the manifold guide 410 to drive the sliding plate 612 in the E direction. This is one example of an automated activation of the sliding plate 612 to push the sliding plate 612 into the engagement configuration, and other suitable activation mechanisms may be used. To accomplish a time delay, a mechanical watch mechanism or electromechanical software control may be incorporated into the drug delivery device.

Looking to FIGS. 14-18, illustrated is another embodiment of an insertion mechanism 654. The insertion mechanism 654 is similar to the insertion mechanism 54 described above, except for the manner in which a manifold guide 710 is connected and disconnect to a hub 734. Elements of the insertion mechanism 654 depicted in FIGS. 14-18 which are similar to the elements of the insertion mechanism 54 are designated by the same reference numeral, incremented by 600. A description of many of these elements is abbreviated or even eliminated in the interest of brevity. Furthermore, the insertion mechanism 654 may be incorporated into a drug delivery device such as the drug delivery device 10 depicted in FIG. 1.

As illustrated in FIGS. 14-18, the manifold guide 710 may be rotatable relative to the hub 734. The hub 734 includes rigid tabs 766a and 766b with hooks 837a and 837b disposed at the distal ends 824a and 824b of the tabs 766a and 776b. The hooks 837a and 837b are operatively coupled with first and second shoulders 828 and 830 of the manifold guide 710, connecting the hub 734 and the manifold guide 710. The hooks 837a and 837b engage the bottom surface 832 of the first and second shoulders 828 and 830 of the manifold guide 710 such that the manifold guide 710 effectively pulls the hub 734 via the hooks 837a and 837b when the insertion mechanism 654 is activated. The hub 734 and the manifold guide 710 disconnect when the hooks 837a and 837b of the rigid tabs 766a and 766b decouple from the first and second shoulders 828 and 830 of the manifold guide 710. In the illustrated embodiment, the hub 734 and the manifold guide 710 disconnect when the manifold guide 710 rotates relative to the hub 734 in the D direction, causing the hooks 837a and 837b of the rigid tabs 766a and 766b to move out from under the bottom surface 832 of the shoulders 828 and 830.

Figures 15, 16:
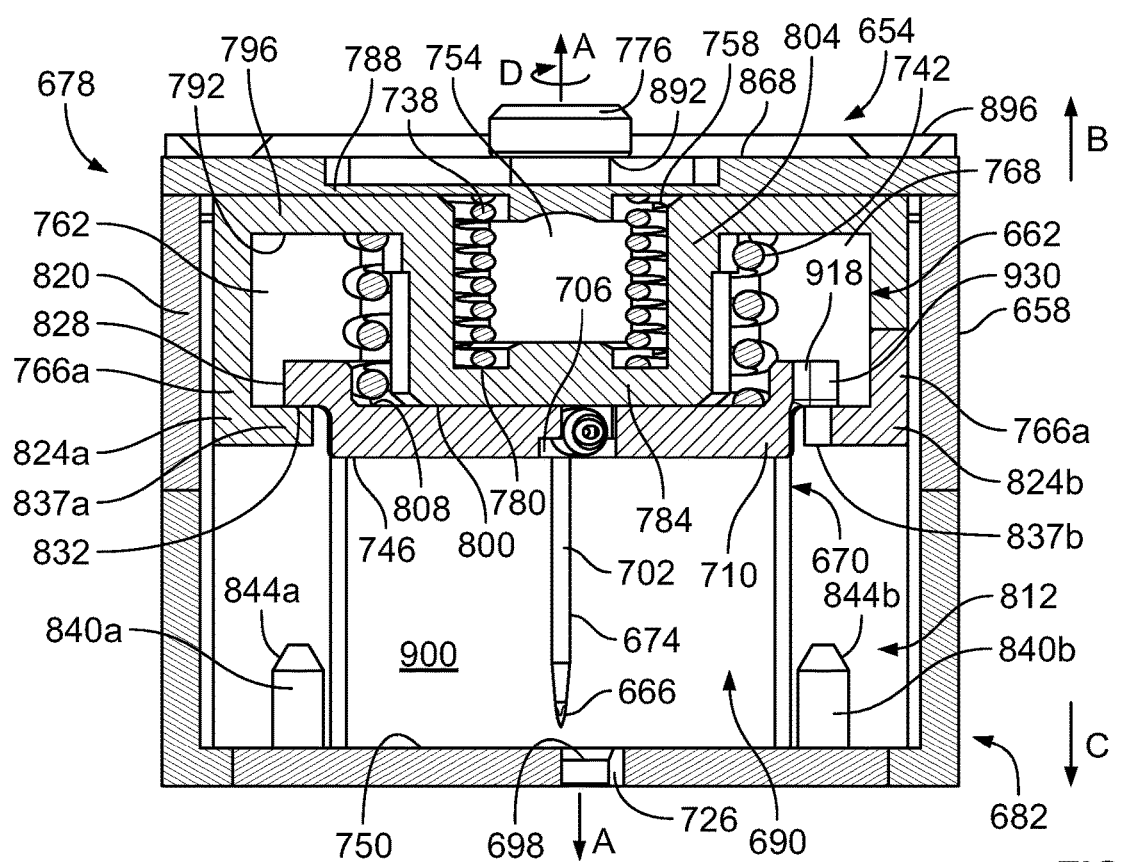
FIG. 15 illustrates a cross-sectional view take from line 15-15 of the insertion mechanism of FIG. 14.
FIG. 16 illustrates a cross-sectional view take from line 16-16 of the insertion mechanism of FIG. 14.
Figure 17:
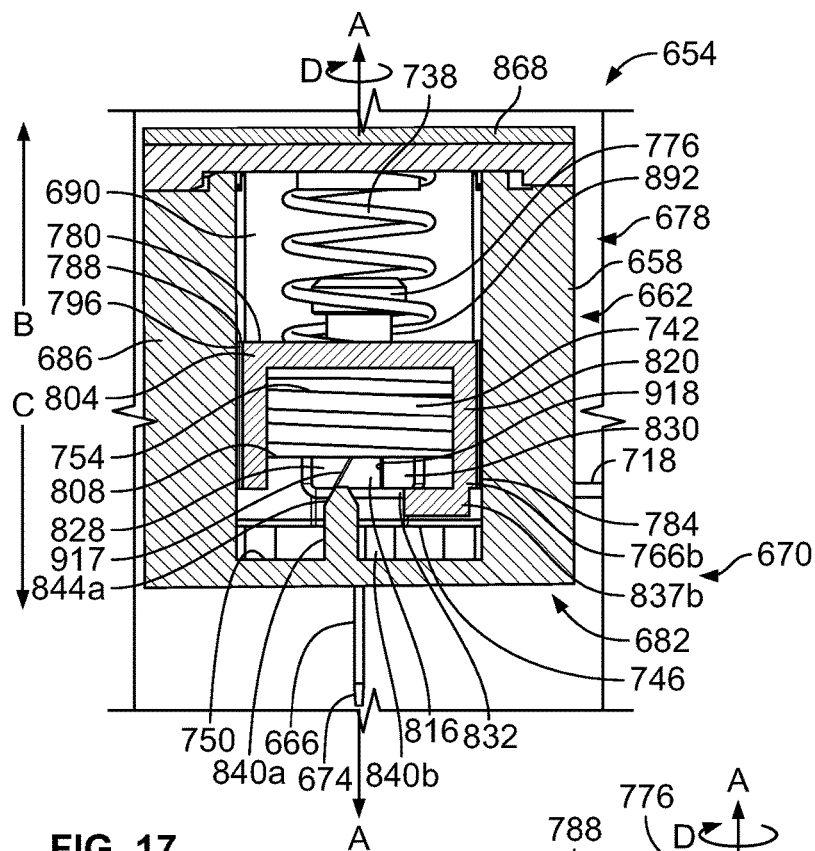
FIG. 17 illustrates the insertion mechanism of FIG. 16 in a position between the pre-fired configuration and an inserted configuration.
Figure 18:
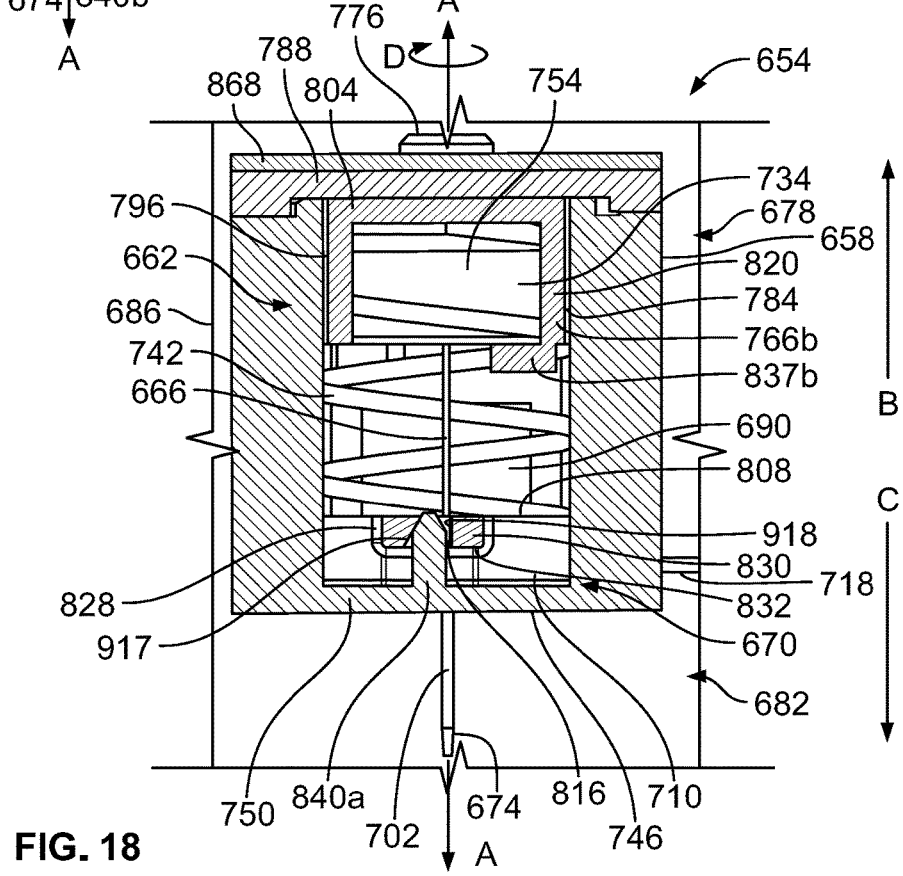
FIG. 18 illustrates the insertion mechanism of FIG. 16 in a retracted configuration.

The disconnect member 812 may include release pins 840a and 840b disposed at the distal end 682 of the housing 658. Each pin 840a and 840b may be aligned with an aperture 816 of the manifold guide 710. Each of the apertures 816 is defined by the space between the first and second shoulders 828 and 830. As shown in FIGS. 16-18, each of the apertures 816 has an asymmetrical cross-section defined by an angled interior edge 917 of the first shoulder 828 and a straight interior edge 918 of the second shoulder 830. The interior edges 917 and 918 further define a bottom end 920 of the aperture that is offset from a top end 922. The release pins 840a and 840b include tapered ends 844a and 844b that are angled to match the angled interior edge 917 of the aperture 816. As the manifold guide 710 and hub 734 move from the first position to the second position, the tapered ends 844a and 844b of the pins 840a and 840b enter the bottom ends 902 of the apertures 816 and slide against the angled interior surface 917. In FIGS. 17 and 18, the manifold guide 710 moves toward the second position causing the shoulder 830 of the manifold guide 710 to rotate away or slide out of contact with the hook 837b of the rigid tab 766b. When the insertion mechanism 654 is in the retracted configuration shown in FIG. 18, the pin 840a and 840b is disposed through the aperture 816, the manifold guide 710 is rotated out of connection with the hub 734, the retraction biasing member 742 is expanded, and the hub 734 is in the first hub position. While not illustrated in each of FIGS. 14-18, the activation member may be the same or different from the activation member illustrated in previous embodiments.

FIGS. 19 and 20 illustrate yet another embodiment of an insertion mechanism 954. The insertion mechanism 954 is similar to the insertion mechanism 54 described above, except for the manner in which a manifold guide 1010 is connected and disconnect to a hub 934. Elements of the insertion mechanism 954 depicted in FIGS. 19 and 20 which are similar to the elements of the insertion mechanism 54 are designated by the same reference numeral, incremented by 900. A description of many of these elements is abbreviated or even eliminated in the interest of brevity. Furthermore, the insertion mechanism 954 may be incorporated into a drug delivery device such as the drug delivery device 10 depicted in FIG. 1.

As shown in FIGS. 19 and 20, a spring-biased retaining member 1220*a* and 1220*b*, also referred herein as a retaining member, is provided for each deformable tab 1066*a* and 1066*b* to initially retain the deformable tab 1066*a* and 1066*b* to connect the hub 1034 and the manifold guide 1010. Each retaining member 1220*a* and 1220*b* is disposed between an outer portion 1222 of the manifold guide 1010 and the deformable tab 1066*a* and 1066*b* of the hub 1034. The deformable tab 1066*a* and 1066*b* is initially in contact with the shoulders 1028 and 1030 of the manifold guide 1010. In the pre-fired configuration depicted in FIG. 19, the retaining members 1220*a* and 1220*b* may each be spring-biased to a first rotational position where the retaining members 1220*a* and 1220 contact, respectively, the deformable tabs 1066*a* and 1066*b*. As a result, the deformable tabs 1066*a* 1066*b* may be retained in a position where the distal ends 1124*a* and 1124*b* of the deformable tabs are engaged with angled bottom surfaces 1032*a* and 1032*b* of the shoulders 1028 and 1030 of the manifold guide 1010. The retaining members 1220*a* and 1220*b* initially hold the deformable tabs 1066*a* and 1066*b* against the manifold guide 1010, thereby preventing or inhibiting the deformable tabs 1066*a* and 1066*b* from expanding outwardly relative to the manifold guide 1010 as a result of the biasing force provided by the retraction biasing member 1042. Accordingly, the retaining members 1220*a* and 1220*b* may prevent the manifold guide 1010 from prematurely disconnecting from the hub 1034. As the manifold guide 1010 moves to the second position, the retaining members 1220*a* and 1220*b* move with the manifold guide 1010 to retain the deformable tabs 1066*a* and 1066*b* until the disconnect member 1112 engages the retaining members 1220*a* and 1220*b*.

FIG. 20 illustrates the moment in time when the disconnect member 1112 engages the retaining members 1220*a* and 1220*b* to disconnect the manifold guide 1010 and the hub 1034. The disconnect member 1112 includes pins 1140*a* and 1140*b* disposed at the distal end 982 of the housing 958, and each pin 1140*a* and 1140*b* is aligned to engage one of the retaining members 1220*a* and 1220*b* without directly engaging with the manifold guide 1010 or the hub 1034. The pins 1140*a* and 1140*b* engage the retaining members 1220*a* and 1220*b* before the insertion biasing member 1038 reaches the end of its stroke and before the manifold guide 1010 reaches the second position. Shown in this moment, the pins 1140*a* and 1140*b* have caused the retaining members 1220*a* and 1220*b* to rotate in a direction H away from the deformable tabs 1066*a* and 1066*b* to a second rotational position. In this second rotational position, the retaining members 1220*a* and 1220*b* may provide enough clearance for the deformable tabs 1066*a* and 1066*b* to move away from the manifold guide 1010, thereby disconnecting the manifold guide 1010 from the hub 1034. The distal ends 1124*a* and 1124*b* of the deformable tabs 1066*a* and 1066*b* have inclined surfaces 1137*a* and 1137*b* that permit the deformable tabs 1066*a* and 1066*b* to slide out of contact with the angled bottom surfaces 1132*a* and 1132*b* of the shoulders 1128 and 1130 of the manifold guide 1010. The angled bottom surface 1032*a* and 1032*b* of the manifold guide 1010 may be non-parallel to the longitudinal axis A and form an angle of less than 90 degrees relative the longitudinal axis A. In some embodiments, the inclined surface 1137*a* and the inclined surface 1032*a* may form the same, or substantially the same, angle relative to the longitudinal axis A. Similarly, the inclined surface 1137*b* and the angled bottom surface 1032*b* may form the same, or substantially the same, angle relative to the longitudinal axis A. Accordingly, flush engagement of the inclined surfaces 1137*a* and 1137*b* with their corresponding angled bottom surfaces 1032*a* and 1032*b* may be possible. In some embodiments, the spring retaining members 1220*a* and 1220*b* may include spring locks that bias against the release pins 1140*a* and 1140*b* when the retaining members 1220*a* and 1220*b* engage with the pins 1140*a* and 1140*b*. The spring force for each retaining member 1220*a* and 1220*b* is overcome by the spring force of the insertion biasing member 1038 so that there is limited resistance to rotate the retaining members 1220*a* and 1220*b*. In other embodiments, the spring retaining members 1220*a* and 1220*b* may be hinged doors that rotate in a direction H to release the deformable tabs 1066*a* and 1066*b* when displaced by the release pins 1140*a* and 1140*b*.

Turning to FIGS. 21-25, depicted is another embodiment of an insertion mechanism 2054. The insertion mechanism 2054 is similar to the insertion mechanism 54 described above, except for the manner in which a manifold guide 2010 is connected and disconnected to a hub 2034. Also, there are some structural variations in the trocar and cannula assemblies 2062 and 2070 relative to those used in conjunction with the insertion mechanism 54. Elements of the insertion mechanism 2054 depicted in FIGS. 21-25 which are similar to the elements of the insertion mechanism 54 are designated by the same reference numeral, incremented by 2000. A description of many of these elements is abbreviated or even eliminated in the interest of brevity. Furthermore, the insertion mechanism 2054 may be incorporated into a drug delivery device such as the drug delivery device 10 depicted in FIG. 1.

Figure 21:
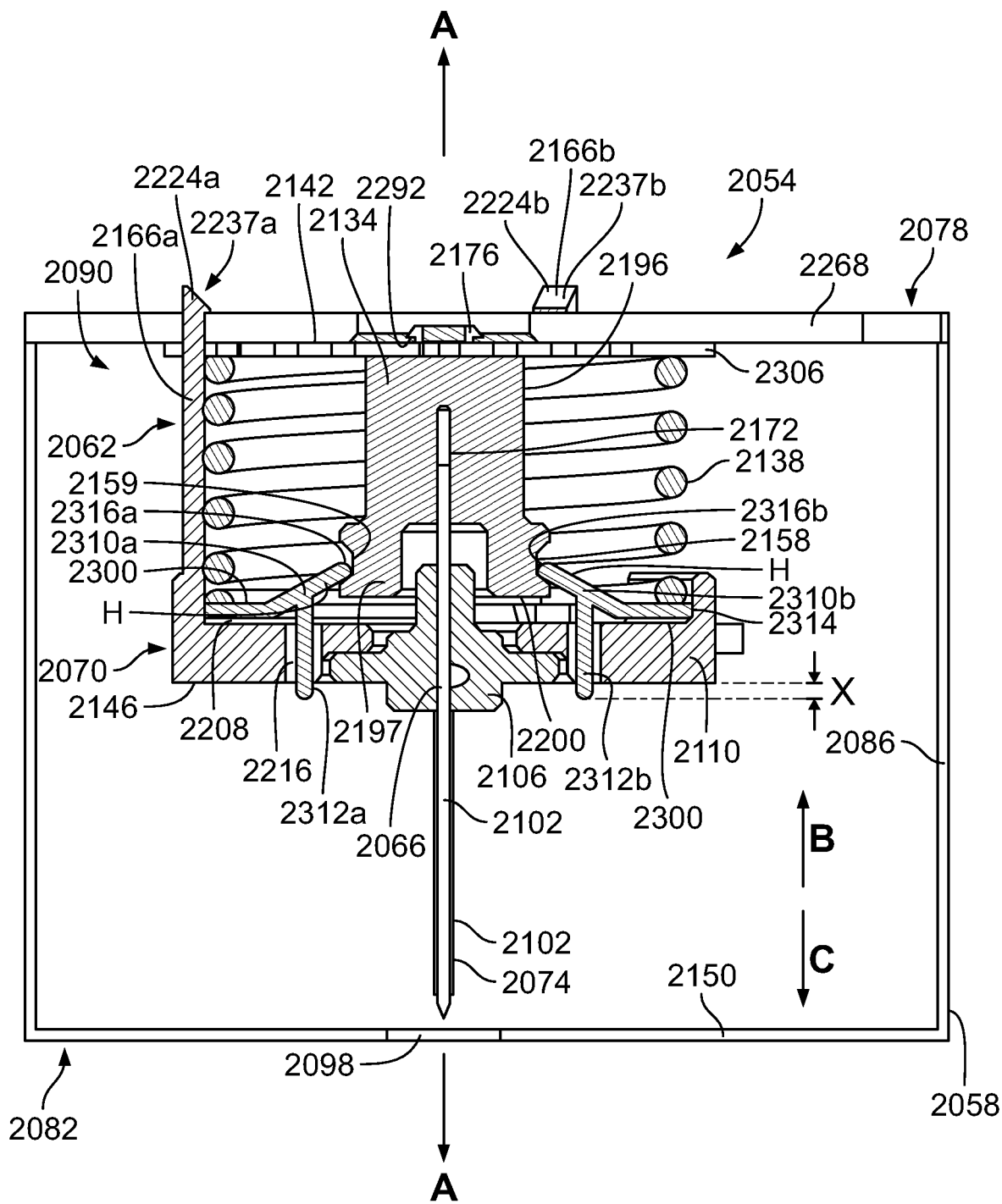
FIG. 21 illustrates a partial cross-sectional view of another embodiment of an insertion mechanism in a pre-fired configuration.
Figure 22:
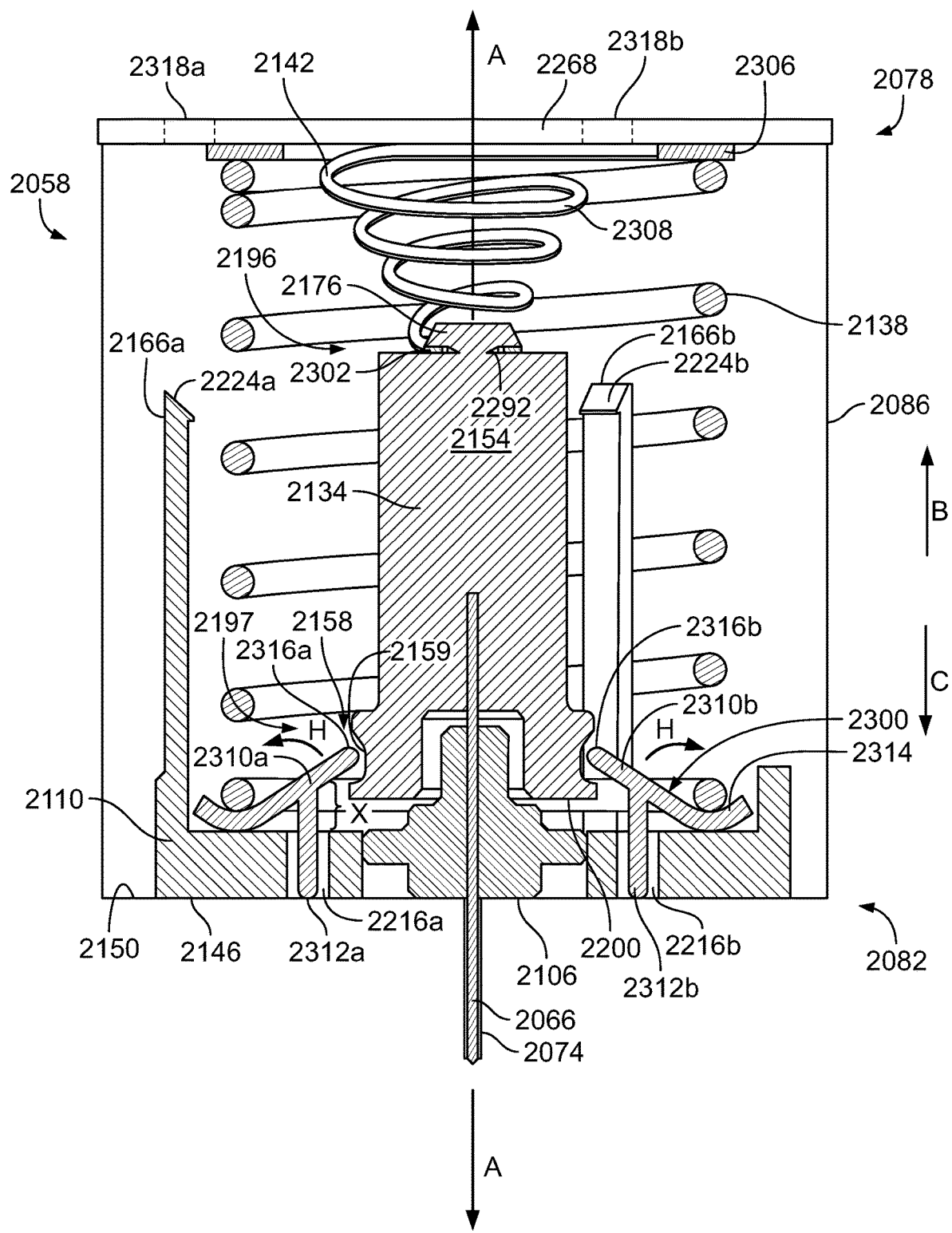
FIG. 22 partially illustrates the insertion mechanism of FIG. 21 in an inserted configuration.

The cannula assembly 2070 includes the cannula 2074, the manifold guide 2110 carrying the manifold 2106, a deformable ring 2300, and the insertion biasing member 2138. The trocar assembly 2062 includes the trocar 2066, the hub 2134 carrying the trocar 2066, and the retraction biasing member 2142. The hub 2314 includes a flanged knob 2176 defined by the groove 2292 at its proximal end 2196 and an annular channel 2158 disposed at a distal end 2197. The flanged knob 2176 is coupled to the retraction biasing member 2142. The hub 2134 is removably connected to the manifold guide 2110 via the deformable ring 2300, which deforms to disconnect the hub 2340 from the manifold guide 2110 and permit the trocar assembly 2062 to retract after the trocar 2066 and cannula 2074 are inserted through the opening 2098 of the housing 2058. The deformable ring 2300 moves with the manifold guide 2110 when the insertion mechanism 2054 occupies the pre-fired configuration in FIG. 21 and the inserted configuration in FIG. 22. The manifold guide 2110 includes deformable tabs 2166*a* and 2166*b* that engage the housing 2058 in the pre-fired configuration and are configured to disengage from the housing 2058 and release the insertion biasing member 2138 when the insertion mechanism 2054 is activated. FIGS. 21 and 22 only partially illustrate the insertion mechanism 2054 for purposes of clarity.

In the pre-fired configuration shown in FIG. 21, the retraction biasing member 2142 is initially retained in a non-energized state between the hub 2134 and the proximal end 2078 of the housing 2058. The insertion biasing member 2138 is initially retained in an energized state between the proximal end 2078 of the housing 2058 and the manifold guide 2110. More specifically, the retraction biasing member 2142 is a spring disc with an outer portion 2306 adjacent to the top portion 2268 of the housing 2058 and the insertion biasing member 2138. The insertion biasing member 2138 is a coil spring and is retained specifically between the outer portion 2306 of the spring disc 2142 and the deformable ring 2300. The deformable ring 2300 is retained between the insertion biasing member 2138 and the top surface 2208 of the manifold guide 2110. In another embodiment, the coil spring 2138 may be retained between the top portion of the housing 2268 and the top surface 2208 of the manifold guide 2110 where the outer portion 2306 of the spring disc 2142 is fixed to the top portion 2268 of the housing 2058 and the outer edge 2314 of the deformable ring 2300 is fixed to the top surface 2208 of the manifold guide 2110. The insertion mechanism 2054 in this embodiment may facilitate assembly of the insertion mechanism 2054 by providing one, rather than two, energized biasing members.

Figure 23:
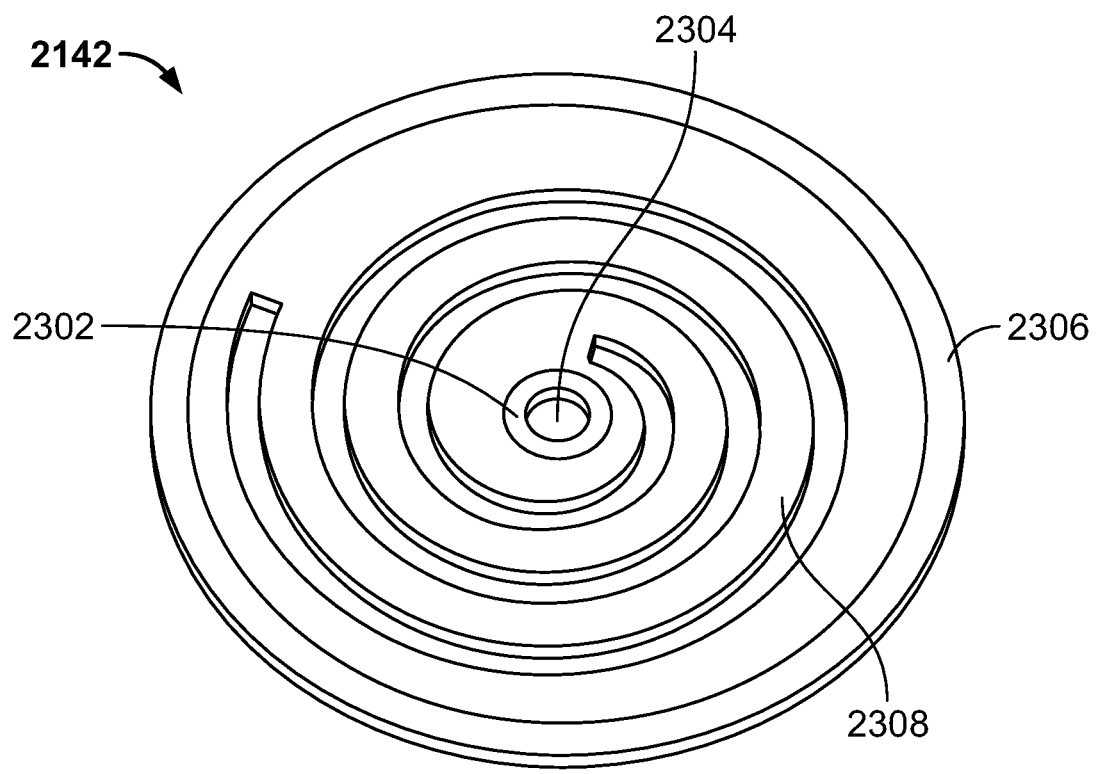
FIG. 23 illustrates a retraction biasing member of the insertion mechanism of FIGS. 21 and 22.

Referring to FIGS. 21, 22, and 23, the flanged knob 2176 is disposed through a central aperture 2304 of the spring disc 2142 to connect the groove 2292 of the hub 2134 with a central portion 2302 of the spring disc 2142. When the insertion biasing member 2138 is released, the insertion biasing member 2138 biases the hub 2134 away from the first hub position of FIG. 21 to the second hub position of FIG. 22. The spring disc 2142 becomes energized when the hub 2134 pulls the central portion 2302 of the spring disc 2142 downward in the distal direction C. As shown in FIG. 22, the outer portion 2306 of the spring disc 2142 remains adjacent to the top portion 2268 of the housing 2058, and a spiral 2308 of the spring disc 2142 is partially arranged within the spring coil of the insertion biasing mechanism 2138. As the manifold guide 2110 moves from the first position to the second position, the spring disc 2142 becomes increasingly energized until the manifold guide 2110 and hub 2134 disconnect and the spring disc 2142 returns to its non-energized state.

Figure 24:
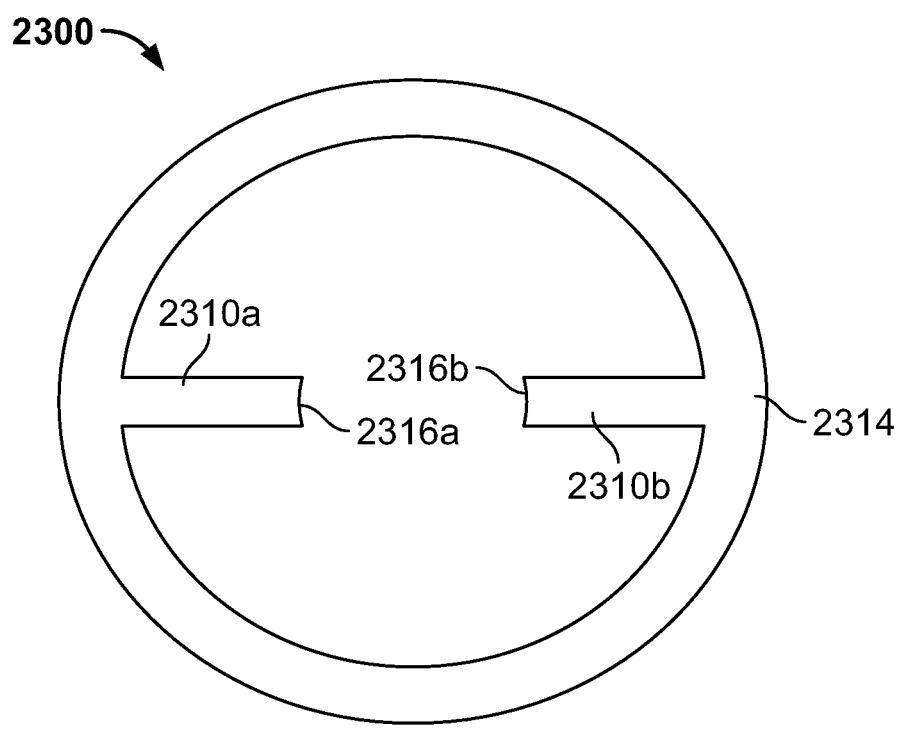
FIG. 24 illustrates a top view of a deformable ring of the insertion mechanism of FIG. 21.

As shown in FIGS. 21, 22 and 24, the deformable ring 2300 of the cannula assembly 2070 is arranged between the insertion biasing member 2138 and the top surface 2208 of the manifold guide 2110. First and second engaging arms 2310a and 2310b extend from an outer edge 2314 of the deformable ring 2300. The outer edge 2314 provides a spring seat for the insertion biasing member 2138, and distal ends 2316a and 2316b of the engaging arms 2310a and 2310b are shaped to match the curvature of a circumferential surface 2159 of the hub 2134. In the pre-fired configuration of FIG. 21, the distal ends 2316a and 2316b of the engaging arms 2310a and 2310b are located within the channel 2158 and contact the circumferential surface 2159 of the hub 2134. First and second legs 2312a and 2312b of the deformable ring 2300 extend downward from a side opposite the spring seat and are disposed in the apertures 2216a and 2216b formed in the manifold guide 2110. The apertures 2216 extend from the top surface 2208 through the bottom surface 2142 of the manifold guide 2110, are wide enough to axial movement of the legs 2312a and 2312b. The deformable ring 2300 may be customized according to desired application to meet the requirements of varying insertion mechanism. For example, a different embodiment may include more than two engaging arms with a preferred thickness to better grip or connect the deformable ring and the hub. In yet another embodiment, the material of the deformable ring may be determined based on the spring force of the insertion biasing member 2138, the spring force of the retraction biasing member 2142, the configuration of the hub 2134, and/or the configuration of the manifold guide 2110.

In the pre-fired configuration, the legs 2312a and 2312b extend beyond the bottom surface 2146 of the manifold guide 2110 by an offset distance x until the manifold guide 2110 occupies the second position. As such, the legs 2312a and 2312b contact the bottom surface 2150 of the housing 2058 before the manifold guide 2110 occupies the second position. As the manifold guide 2110 moves the distance x to occupy the second position, the bottom surface 2150 of the housing 2058 sufficiently impacts the legs 2312a and 2312b, causing the deformable ring 2300 to deform and disconnect the manifold guide 2110 and the hub 2134. By comparison to FIG. 21, the legs 2312a and 2312b illustrated in FIG. 22 are located the offset distance x in the proximal direction B and are in contact with the bottom surface 2150 of the housing 2058. The axial movement of the legs 2312a and 2312b within the apertures 2216a and 2216b combined with the rigid connection of the outer edge 2314 of the deformable ring 2300 and the manifold guide 2110 cause the engaging arms 2310a and 2310b to deform and bend away from the channel 2153 in the H direction. During deformation, the engaging arms 2310a and 2310b expand radially outwardly relative to the hub 2134 and disconnect the hub 2134 from the manifold guide 2110. The deformable ring 2300 remains between the top surface 2208 of the manifold guide 2110 and the insertion biasing member 2138 when the cannula assembly 2070 is retracted. In another embodiment, the deformable ring 2300 may not include legs 2312a and 2312b disposed through apertures 2316a and 2316b of the manifold guide 2110. Rather, when the manifold guide 2110 reaches the second manifold position, the deformable ring 2300 may still deform to disconnect the hub 2134 from the manifold guide 2110. In yet another embodiment, the geometry and material properties of the deformable ring 2300 may be adjusted so that the retraction force of the retraction biasing member 2142 overcomes a force of engagement between the engaging arms 2310a and 2310b and the channel 2158 of the hub 2134 at a desired release point.

Figure 25:
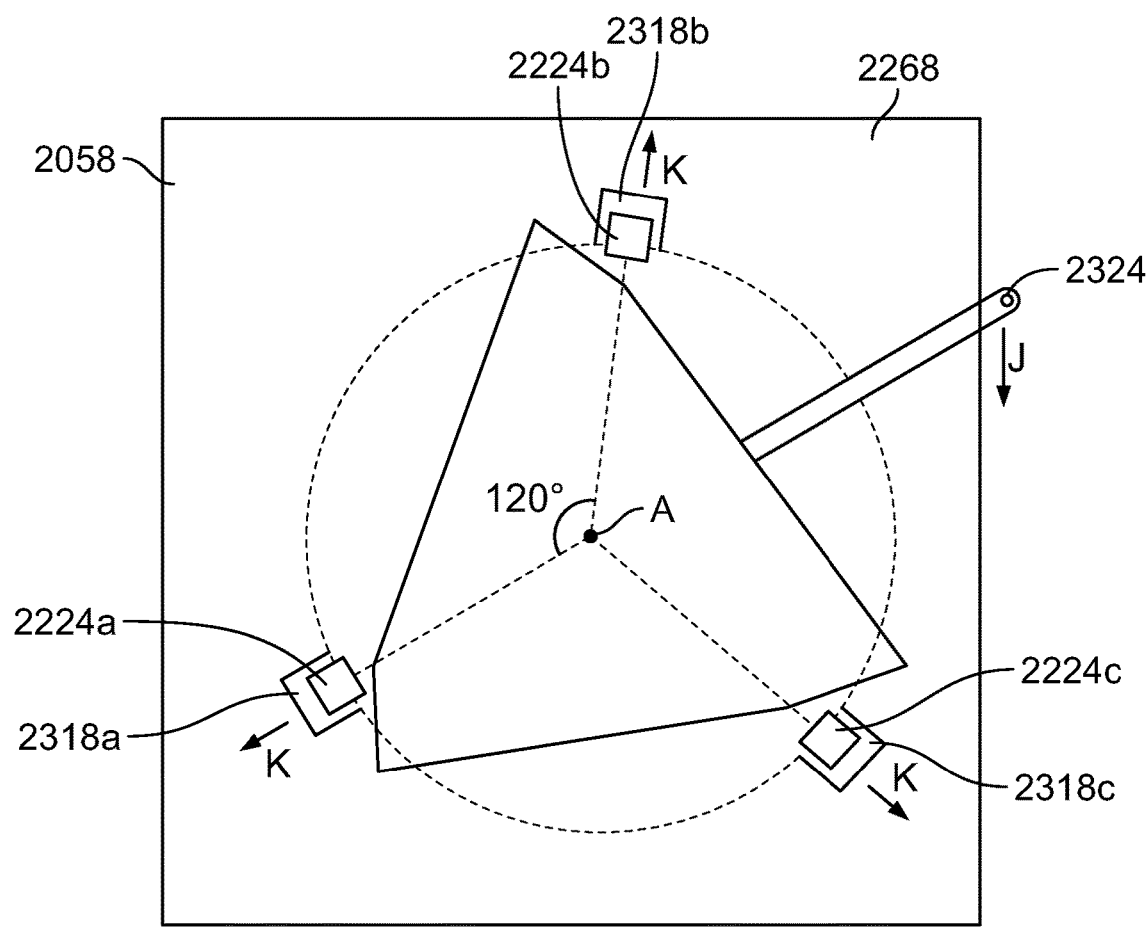
FIG. 25 illustrates a top view of an activation member of the insertion mechanism of FIG. 21.

The activation member 2076 will now be described with reference to FIGS. 21 and 25. The upward extending deformable tabs 2166a and 2166b of the manifold guide 2110 include respective distal ends 2224a and 2224b disposed through the top portion 2268 of the housing 2058. In FIG. 25, the manifold guide 2110 includes three deformable tabs equally spaced apart, the distal ends 2224a, 2224b, and 2224c of the deformable tabs are shown disposed through three corresponding apertures 2318a, 2318b, and 2318c formed in the top portion 2268 of the housing 2058. The inclined surfaces 2237a, 2237b, and 2237c of the distal ends 2224a, 2224b, and 2224c are formed to catch onto or engage the top portion 2268 of the housing 2058, connecting the manifold guide 2110 and the housing 2058 in the pre-fired configuration. In this embodiment, the activation member 2076 includes a cam 2320 that rotates in a direction J when actuated or triggered by lever 2324. The cam 2320 generally has a triangular shape but for clipped ends 2326a, 2326b, and 2326c that are shaped to slide against the distal ends 2224a, 2224b, and 2224c of the deformable tabs when the cam rotates 120 degrees. As the clipped ends 2326a, 2326b, and 2326c of the cam 2320 slide against the distal ends 2224a, 2224b, and 2224c of the deformable tabs, the deformable tabs are pushed outwardly in a direction K, disengaging the distal ends 2224a, 2224b, and 2224c from the top portion 2268 of the housing 2058 which fall through the corresponding apertures 2318a, 2318b, and 2318c. Once the distal ends 2224a, 2224b, and 2224c are cleared from the top portion 2268 of the housing 2058, the insertion biasing member 2138 is released and moves the manifold guide 2110 in the distal direction C. The lever 2324 may be rotated by a coupled movement from the actuator 28 accessible from the exterior of the main housing 30 of the drug delivery device 10 of FIG. 1. In one embodiment, the actuator 28 may be a linear activation switch that permits a patient to slide a button across the exterior surface of the housing 30 of the drug delivery device 10 to activate the lever 2324. In another embodiment, the actuator 28 may be a depressible button configured to release a spring-loaded catch that pushes the lever in the direction J when the button is pushed. To avoid accidental pressure/release of the button prior to attaching the device 10 to patient, the spring-loaded catch may be initially locked until the device 10 is physically applied to the patient. A mechanical on-body sensor may unlock the spring-loaded catch when physical application of the device 10 is sensed by the on-body sensor.

The methods and mechanism described herein provide advantages over known insertion devices, such as simpler design, increased reliability, decrease in patient discomfort and anxiety, increase in accuracy, and decrease in terms of costs and time of manufacturing. In particular, the insertion mechanisms 54, 354, 654, 954, and 2054 of the present disclosure may be easily adapted for use with many different wearable drug delivery devices and may be customized for specific patient populations. The insertion mechanisms 54, 354, 654, 954, and 2054 may be implemented in a wide variety of wearable drug delivery devices having different drive mechanisms, different forms, and for different drugs. The operation of the insertion mechanisms 54, 354, 654, 954, and 2054, and particularly the trocar assemblies 62, 362, 662, 962, and 2062 and cannula assemblies 70, 370, 670, 970, and 2070 are not limited in operation or function by the drive mechanism 24, the activation member 76, 376, or 2076, or the form of the drug delivery device 10. Further, the insertion mechanisms 54, 354, 654, 954, and 2054 may be adapted or customized to minimize pain for specific patients and patient populations. For example, the travel distance between the first position and the second position of the trocar assemblies 62, 362, 662, 962, and 2062 and the cannula assemblies 70, 370, 670, 970, and 2070 may be minimized. Additionally, the spring force of the insertion biasing members 138, 438, 738, 1038, and 2138, the mass of the manifold guides 110, 410, 710, 1010, and 2110, and/or the mass of the manifolds 106, 406, 706, 1006, and 2106 may be decreased to lessen the insertion impact force imparted onto the patient.

In the embodiments illustrated in FIGS. 2-20, the ratio of the insertion biasing member spring force to retraction biasing member spring force may be approximately (e.g., ±10%) 0.77. Furthermore, in these embodiments, the insertion biasing members 138, 438, 738, and 1038 may have a spring force in a range of approximately (e.g., ±10%) 4 N to 15 N and the retraction biasing members 142, 442, 742, and 1042 may have a spring force in a range of approximately (e.g., ±10%) 6 N to 35 N, which may achieve an insertion time of approximately (e.g., ±10%) 0.01 seconds or less, an injection depth of approximately (e.g., ±10%) 8 mm, and a total device height of approximately (e.g., ±10%) 25 mm. In the embodiment illustrated in FIGS. 21-25, the ratio of the retraction biasing member spring force to insertion biasing member spring force may be approximately (e.g., ±10%) 0.77. The insertion biasing member 2138 may have a spring force in a range of approximately (e.g., ±10%) 4 N to 15 N and the retraction biasing member 2142 may have a spring force in a range of approximately (e.g., ±10%) 2 N to 12 N, which may achieve an insertion time of approximately (e.g., ±10%) 0.01 seconds or less, an injection depth of approximately (e.g., ±10%) 8 mm, and a total device height of approximately (e.g., ±10%) 25 mm.

Figure 28:
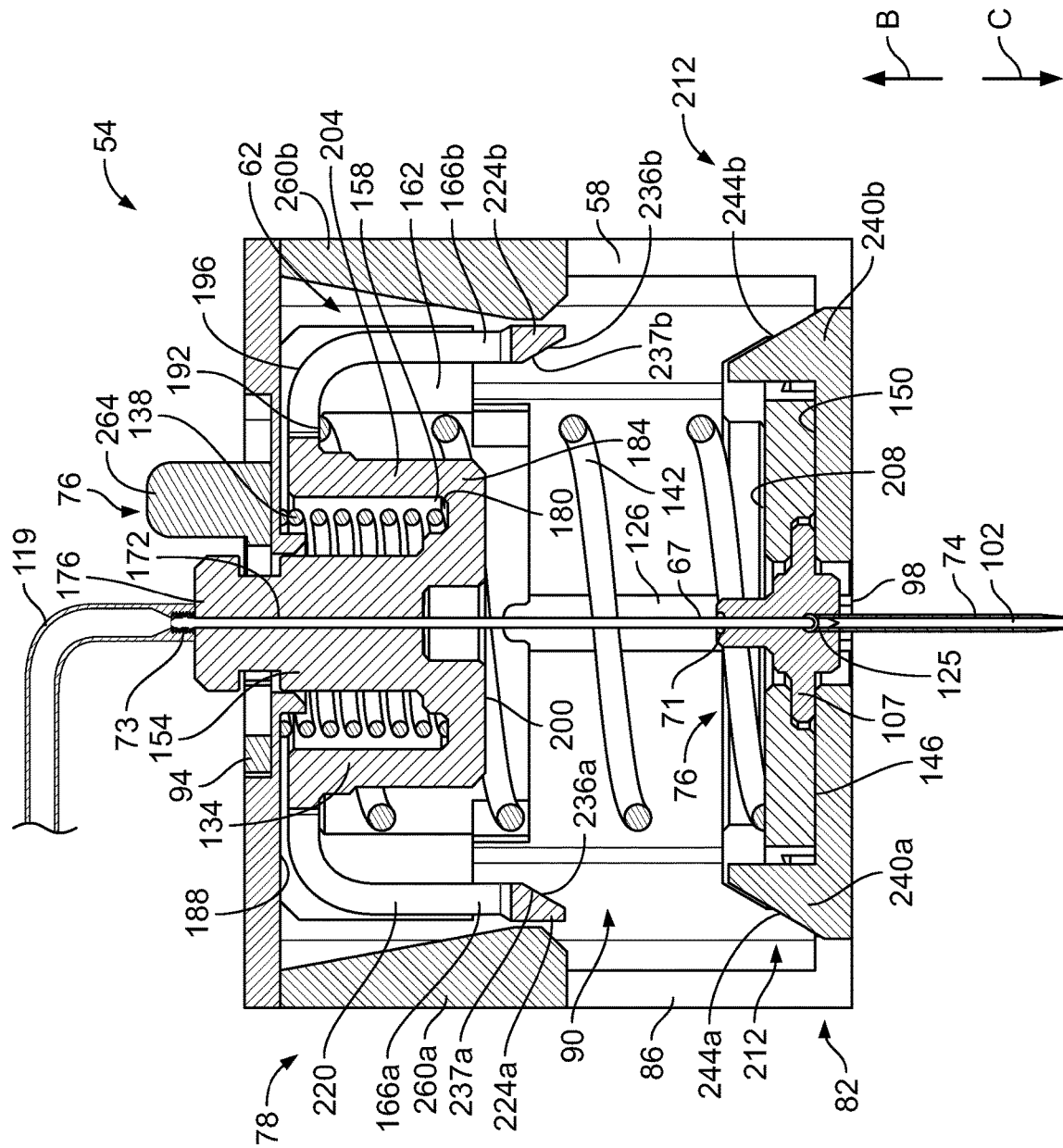
FIG. 28 illustrates a different embodiment of an insertion mechanism in a retracted configuration.
Figure 29:
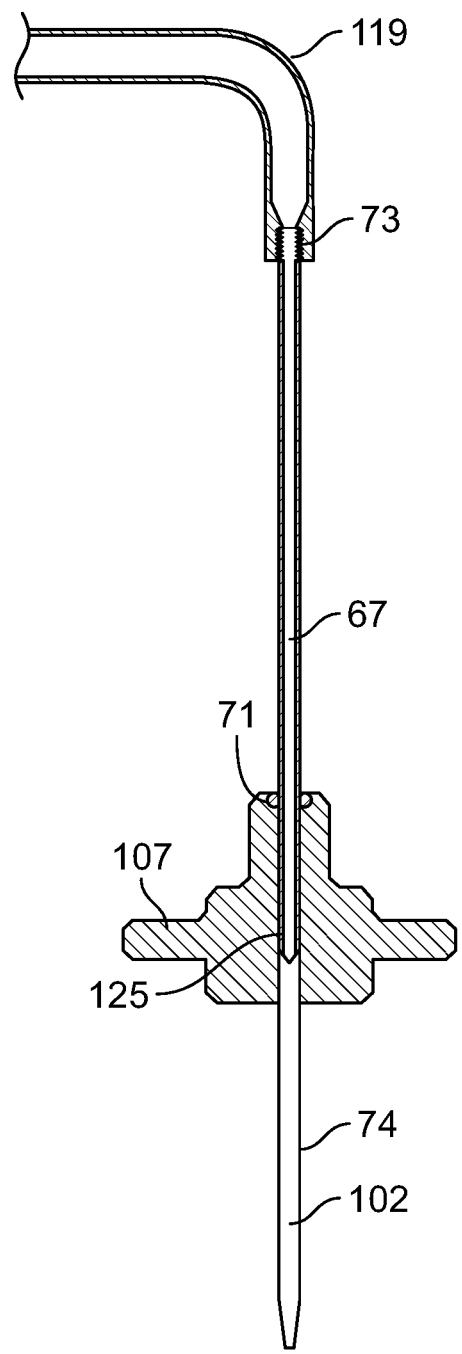
FIG. 29 illustrates a cross-sectional view of cannula guide, cannula, hollow needle, and a fluid pathway connector of the insertion mechanism of FIG. 28.

The insertion mechanisms 54, 354, 654, 954, and 2054 may also increase patient comfort and decrease potential patient anxiety. For example, the insertion mechanisms 54, 354, 654, 954, and 2054 may automatically operate and the trocar assemblies 62, 362, 662, 962, and 2062 and may be configured to retract the trocar 66, 366, 666, 966, or 2066 with little delay after insertion of the cannula 74, 374, 674, 974, or 2074 in the patient, minimizing time the trocar is disposed in the patient's body. In conventional methods and mechanisms, patients may be required to insert the trocar or rigid needle into themselves as they advance a button into the device. This type of insertion mechanism may be a cause of anxiety or intimidation to the patient because they are controlling the insertion of the trocar with the advancement of the button. Additionally, known methods and mechanisms include rigid needles combined with an external safety guard that may remain in the patient's skin when the patient is removing the wearable device. In contrast, the disclosed wearable drug delivery device may have a smaller injection site and can be configured to retract the trocar 66, 366, 666, 966, or 2066 and the cannula 74, 374, 674, or 2074 before the patient removes the wearable device. In another example, the insertion mechanisms 54, 354, 654, 954, and 2054 may not include a separate manifold 106, 406, 706, 1006, and 2106 and manifold guide 110, 410, 710, 1010, and 2110, but instead may include a cannula guide 107 that carries the cannula 74, 374, 674, 974, or 2074 during drug delivery. The trocar 66, 366, 666, 966, or 2066 may be replaced with a hollow needle (e.g. the hollow needle 67 as illustrated in FIGS. 28 and 29) that is fluidly connected to the fluid pathway connector 22 and the cannula 74, 374, 674, 974, or 2074. As such, the drug may be delivered through the hollow needle and into the cannula 74 for drug delivery to the patient. However, the scope of the present disclosure is not limited to these or any other benefits and advantages described herein, and other benefits and advantages may result from the disclosed embodiments and any modifications thereto in accordance with principles of the present disclosure.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933;

5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12 of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed:

1. A wearable drug delivery device comprising:
   a main housing;
   a container disposed in the main housing;
   an insertion mechanism disposed in the main housing;
   a fluid pathway connector defining a sterile fluid flowpath between the container and the insertion mechanism at least during drug delivery; and
   the insertion mechanism including
   a trocar or hollow needle,
   a cannula axially aligned with the trocar or hollow needle at least during operation of the insertion mechanism and having a hollow interior,
   an insertion mechanism housing having a proximal end and a distal end,
   a cannula guide carrying the cannula and movable relative to the insertion mechanism housing between a first position and a second position, the cannula guide located at the distal end of the insertion mechanism housing when in the second position,
   a hub carrying the trocar or hollow needle and removably connected to the cannula guide, the hub including a first groove defining a spring seat and a second groove,
   an insertion biasing member initially retained in an energized state in the first groove and being positioned between the proximal end of the insertion mechanism housing and the hub, the insertion biasing member adapted to exert a force on the spring seat to urge the hub towards the distal end of the insertion mechanism housing, and
   a retraction biasing member retained in the second groove and being positioned between the hub and the cannula guide.

2. The wearable drug delivery device of claim 1, further comprising a manifold configured to fluidly connect the hollow interior of the cannula and the fluid pathway connector, and wherein the cannula guide is a manifold guide.

3. The wearable drug delivery device of claim 2, comprising a disconnect member configured to disconnect the manifold guide and the hub when the manifold guide moves to the second position, thereby allowing the retraction biasing member to move the hub in a proximal direction.

4. The wearable drug delivery device of claim 3, comprising a deformable tab initially connecting the manifold guide and the hub, the deformable tab engaging the disconnect member when the manifold guide occupies the second position to disconnect the manifold guide and the hub.

5. The wearable drug delivery device of claim 4, the disconnect member including a rotatable plate disposed at the distal end of the insertion mechanism housing, the rotatable plate including a slot configured to receive the deformable tab when the manifold guide occupies the second position, and the rotatable plate being configured to rotate relative to the manifold guide and deform the deformable tab received in the slot to allow the manifold guide to disconnect from the hub.

6. The wearable drug delivery device of claim 4, the disconnect member including a sliding plate disposed at the distal end of the insertion mechanism housing, the sliding plate configured to displace the deformable tab away from the manifold guide when the sliding plate slides toward the manifold guide and the manifold guide occupies the second position.

7. The wearable drug delivery device of claim 3, comprising:
   a deformable tab initially connecting the manifold guide and the hub;
   a spring-biased retaining member initially retaining the deformable tab in connection with the manifold guide and the hub;
   the spring-biased retaining member configured to engage the disconnect member and rotate relative to the deformable tab during operation of the insertion mechanism, wherein rotation of the spring-biased retaining member allows the deformable tab to move relative to the manifold guide such that the manifold guide disconnects from the hub.

8. The wearable drug delivery device of claim 1, wherein the first groove comprises a first concentric groove and the second groove comprises a second concentric groove.

9. An insertion mechanism for a drug delivery device, the insertion mechanism comprising:
 a trocar or hollow needle;
 a cannula axially aligned with the trocar or hollow needle at least during operation of the insertion mechanism and including a hollow interior;
 a housing having a proximal end and a distal end;
 a cannula guide carrying the cannula and movable relative to the housing between a first position and a second position, the cannula guide being located at the distal end of the housing in the second position;
 a hub carrying the trocar or hollow needle and removably connected to the cannula guide, the hub including a first groove defining a spring seat and a second groove;
 an insertion biasing member initially retained in an energized state in the first groove and being positioned between the proximal end of the housing and the hub, the insertion biasing member adapted to exert a force on the spring seat to urge the hub towards the distal end of the housing; and
 a retraction biasing member retained in the second groove and being positioned between the hub and the cannula guide.

10. The insertion mechanism of claim 9, further comprising a manifold in fluid communication with the hollow interior of the cannula, and wherein the cannula guide is a manifold guide that carries the manifold.

11. The insertion mechanism of claim 10, comprising a disconnect member configured to disconnect the manifold guide and the hub when the manifold guide moves to the second position.

12. The insertion mechanism of claim 11, comprising a deformable tab initially connecting the hub and the manifold guide in an initial state, the deformable tab configured to deform to allow the manifold guide and the hub to disconnect.

13. The insertion mechanism of claim 12, the disconnect member including a rotatable plate disposed at the distal end of the housing, the rotatable plate including a slot configured to receive the deformable tab when the manifold guide occupies the second position, and the rotatable plate being configured to rotate relative to the manifold guide and deform the deformable tab received in the slot to allow the manifold guide to disconnect from the hub.

14. The insertion mechanism of claim 12, the disconnect member including a sliding plate disposed at the distal end of the housing, the sliding plate configured to displace the deformable tab away from the manifold guide when the sliding plate slides toward the manifold guide and the hub occupies the second hub position.

15. The insertion mechanism of claim 9, wherein the first groove comprises a first concentric groove and the second groove comprises a second concentric groove.

* * * * *